United States Patent
Robinson et al.

(10) Patent No.: US 6,462,192 B2
(45) Date of Patent: Oct. 8, 2002

(54) PROCESSES FOR LARGE SCALE PRODUCTION OF TETRAPYRROLES

(75) Inventors: Byron C. Robinson, Santa Barbara; Barbara A. Garcia, Ventura, both of CA (US)

(73) Assignee: Miravant Pharmaceuticals, Inc., Santa Barbara, CA (US)

(*) Notice: Subject to any disclaimer, the term of this patent is extended or adjusted under 35 U.S.C. 154(b) by 72 days.

(21) Appl. No.: 09/767,140

(22) Filed: Jan. 23, 2001
Prior Publication Data
US 2002/0137924 A1 Sep. 26, 2002

(51) Int. Cl.[7] .............................................. C07D 487/22
(52) U.S. Cl. ........................ 540/145; 534/10; 534/11; 534/12; 534/13; 534/14; 534/15; 534/16
(58) Field of Search ........................ 540/145; 534/10, 534/11, 12, 13, 14, 15, 16

(56) References Cited

U.S. PATENT DOCUMENTS

| | | | |
|---|---|---|---|
| 4,649,151 A | 3/1987 | Dougherty et al. | 514/410 |
| 4,877,872 A | 10/1989 | Morgan et al. | 540/145 |
| 4,988,808 A | 1/1991 | Morgan et al. | 540/145 |
| 5,051,415 A | 9/1991 | Morgan et al. | 514/185 |
| 5,109,129 A | 4/1992 | Morgan et al. | 540/145 |
| 5,151,415 A | 9/1992 | Sirany | 514/163 |
| 5,171,749 A | 12/1992 | Levy et al. | 514/410 |
| 5,198,460 A | 3/1993 | Pandey et al. | 514/410 |
| 5,216,012 A | 6/1993 | Morgan et al. | 514/410 |
| 5,225,433 A | 7/1993 | Dougherty et al. | 514/410 |
| 5,250,668 A | 10/1993 | Morgan et al. | 540/145 |
| 5,399,583 A | 3/1995 | Levy et al. | 514/410 |
| 5,424,305 A | 6/1995 | Skalkos et al. | 514/185 |
| 5,438,051 A | 8/1995 | Morgan et al. | 514/185 |
| 5,459,159 A | 10/1995 | Pandey et al. | 514/410 |
| 5,489,590 A | 2/1996 | Gulliya et al. | 514/224.8 |
| 5,512,559 A | 4/1996 | Skalkos et al. | 514/185 |
| 5,514,669 A | 5/1996 | Selman | 514/63 |
| 5,534,506 A | 7/1996 | Morgan et al. | 514/185 |
| 5,552,134 A | 9/1996 | Morgan et al. | 424/9.61 |
| 5,744,598 A | 4/1998 | Skalkos et al. | 540/472 |
| 5,856,515 A | 1/1999 | Therien et al. | 548/400 |
| 6,008,211 A | 12/1999 | Robinson et al. | 514/185 |

*Primary Examiner*—Richard L. Raymond
(74) *Attorney, Agent, or Firm*—Finnegan, Henderson, Farabow, Garrett & Dunner, L.L.P.

(57) ABSTRACT

Processes for the large scale production of tetrapyrrolic compounds useful as photosensitizers in photodynamic therapy, such as meso-formyl porphyrins, meso-acrylate porphyrins, purpurins and benzochlorins. In particular, tin ethyl etiopurpurin (SnET2) and the intermediates necessary for its production without chromatography are disclosed.

149 Claims, No Drawings

PROCESSES FOR LARGE SCALE PRODUCTION OF TETRAPYRROLES

FIELD OF THE INVENTION

The present invention relates to processes especially suitable for the large scale production of tetrapyrrolic compounds, such as meso-formyl porphyrins, meso-acrylate porphyrins, purpurins and benzochlorins. In particular, tin ethyl etiopurpurin (SnET2), sometimes called rostaporfin, and the intermediates necessary for its production without chromatography are disclosed. In addition, much of the chemistry disclosed is applicable to the large scale manufacturing of benzochlorins. Purpurins, benzochlorins and several of the intermediates in the synthesis may be useful as photosensitizers in photodynamic therapy, or as porphyrin building blocks in the synthesis of other porphyrinic materials.

BACKGROUND OF THE INVENTION

Photodynamic therapy is a procedure that uses photoactive (light-activated) drugs to target and destroy diseased cells. Photoactive drugs transform light energy into chemical energy in a manner similar to the action of chlorophyll in green plants. The photoactive drugs are inactive until irradiated by light of a specific wavelength, thereby enabling physicians to target specific groups of cells and control the timing and selectivity of treatment. The result of this process is that diseased or unwanted cells are destroyed with less damage to surrounding normal tissues. For a more detailed description of photodynamic therapy, see U.S. Pat. Nos. 5,225,433, 5,198,460, 5,171,749, 4,649,151, 5,399,583, 5,459,159, and 5,489,590, the disclosures of which are incorporated herein by reference.

A large number of naturally occurring and synthetic dyes are currently being evaluated as potential photoselective compounds in the field of photodynamic therapy. Perhaps the most widely studied class of photoselective dyes in this field are the tetrapyrrolic macrocyclic compounds generally called tetrapyrroles, some of which are shown below.

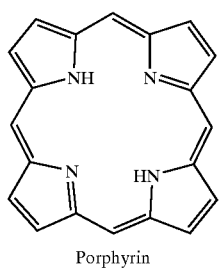

Porphyrin

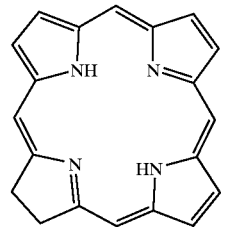

Chlorin

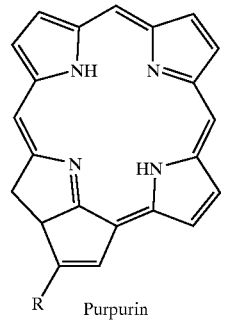

Purpurin

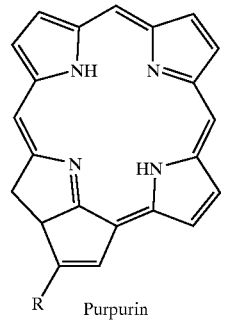

Benzochlorin

In particular, and relevant to this invention, are the chlorin ring systems called purpurins and benzochlorins. Purpurins are a class of chlorin in which an annelated five membered cyclopentenyl ring is directly attached to the reduced pyrrole ring. A notable example of a metallo-purpurin that is showing great promise in the field of photodynamic therapy is tin dichloride ethyl etiopurpurin I (7) (currently prepared by Scheme 1). An older method for synthesis of (7) was outlined in U.S. Pat. No. 5,051,415, the disclosure of which is incorporated herein by reference.

Benzochlorins on the other hand have an annelated benzene ring directly attached to the reduced pyrrole ring. A notable example of a benzochlorin is octaethylbenzochlorin (13) (prepared by Scheme 2) which serves as a starting chlorin for many promising photosensitizers (see U.S. Pat. Nos. 5,552,134; 5,438,051; 5,250,668; 5,109,129; 4,988,808; 5,514,669; 6,008,211; 5,856,515; 5,744,598; 5,512,559; and 5,424,305, the disclosures of which are incorporated herein by reference). To date, very inefficient routes to the synthesis of purpurins and benzochlorin ring systems have been reported and there exists no reported satisfactory method of manufacturing these materials on a large scale.

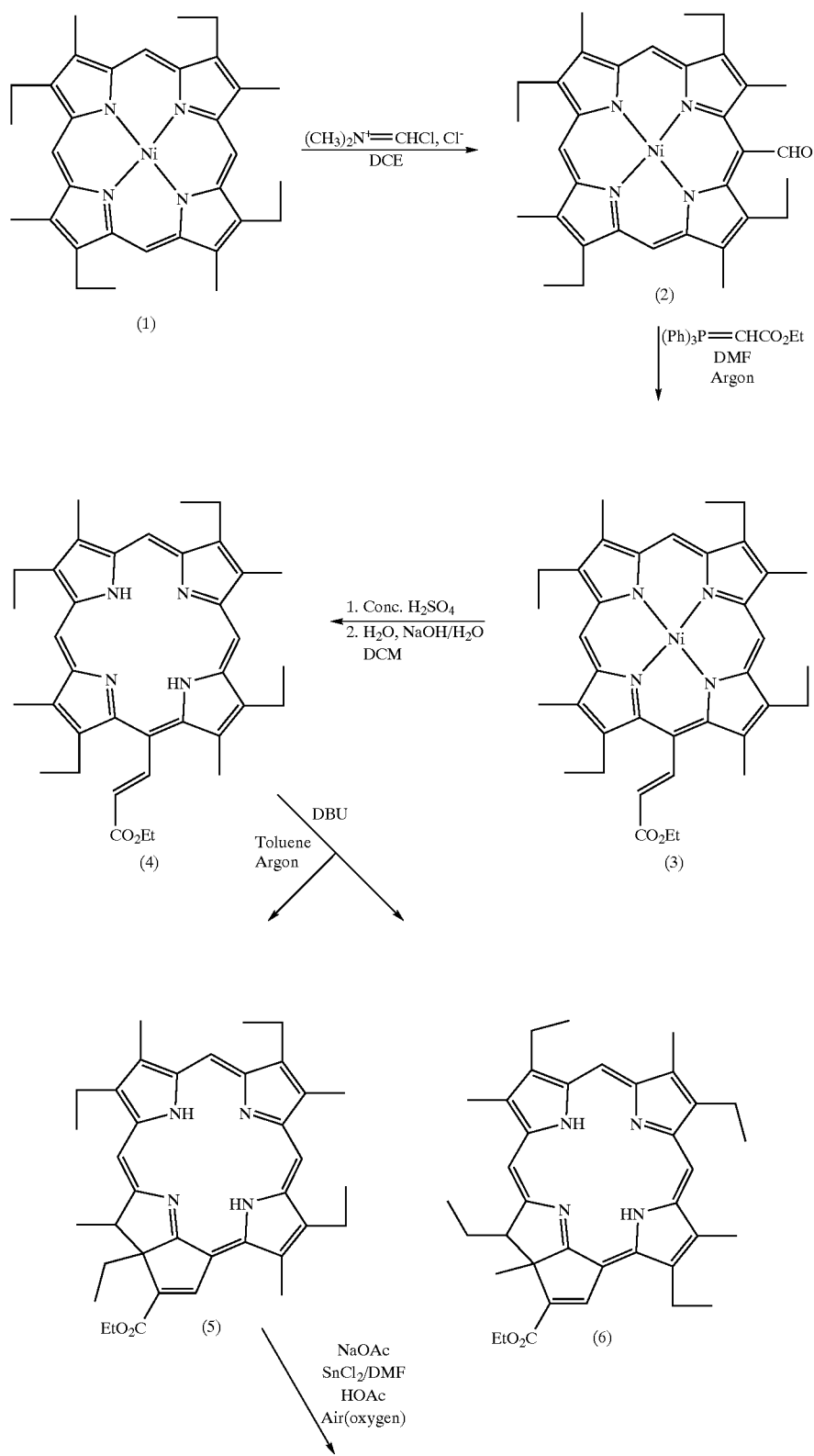
Scheme 1

-continued
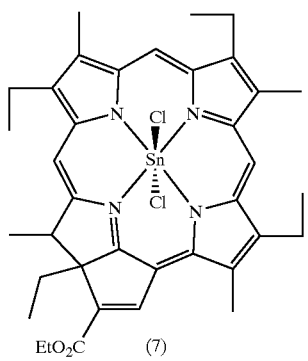
Scheme 2
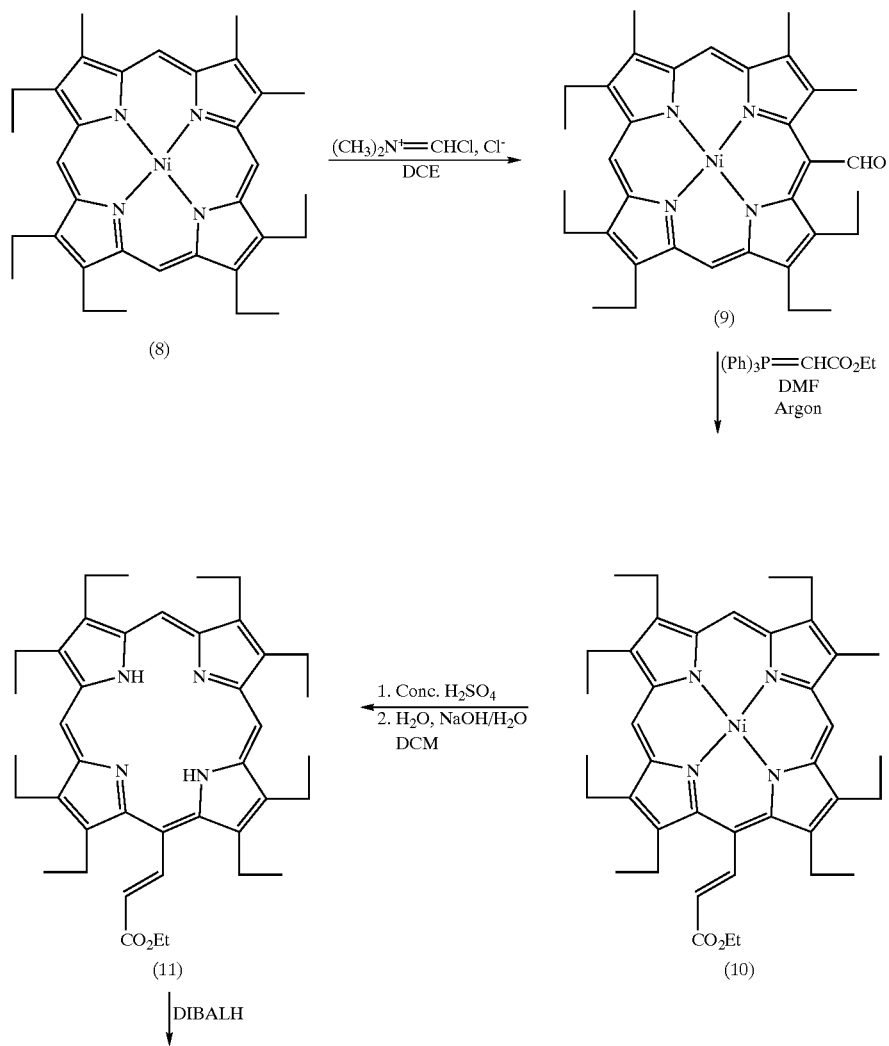

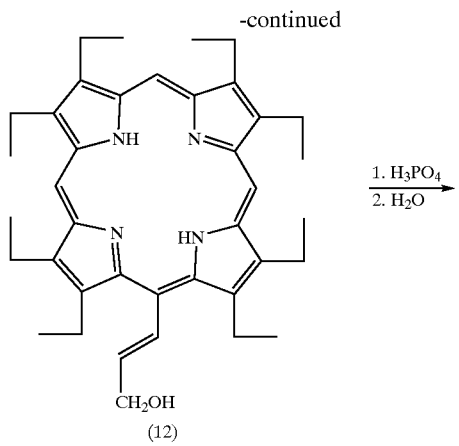

(12)

1. H₃PO₄
2. H₂O

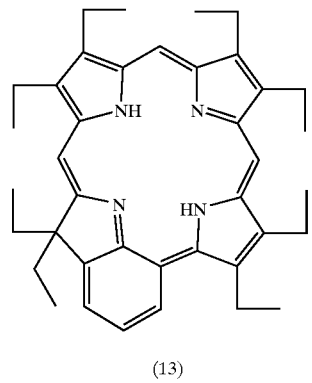

(13)

As a result, a method that enables the synthesis of compounds having these two ring systems, the purpurins and the benzochlorins and their intermediates, on a large scale is of immense value. The present invention provides processes for the large scale preparation of meso-formyl porphyrins, meso-acrylate porphyrins, metal free meso-acrylate porphyrins, metallo-porphyrins, purpurins, metallated purpurins and benzochlorin compounds, the purification steps of which are achieved simply by fractional crystallizations.

It is to be understood that both the foregoing general description and the following detailed description are exemplary and explanatory only and are not restrictive of the present invention as claimed.

DETAILED DESCRIPTION OF THE PREFERRED EMBODIMENTS

The present invention relates to processes for synthesizing meso-formyl porphyrins, β-formyl porphyrins, metallo meso-acrylate porphyrins, metal free meso-acrylate porphyrins, purpurins, metallo-purpurins, metallo-porphyrins and benzochlorins and isolating these compounds simply by fractional crystallization techniques that are amenable to large scale syntheses of such compounds. Processes for the isolation of such compounds will be set forth in the following detailed descriptions of each of the steps of schemes 1 and 2. These processes require no chromatographic separations or additional chemical reactions and are therefore suitable for use on a large scale. The present invention is also particularly relevant to the formylation of metallo-tetrapyrrolic molecules, the reaction of formyl tetrapyrrolic compounds with Wittig reagents, the demetallation of metallo-tetrapyrrolic compounds, the cyclization of meso-acrylate tetrapyrroles to purpurin compounds, the reduction of meso-acrylate tetrapyrrolic compounds, the cyclization of meso-(3-hydroxypropenyl) tetrapyrrolic compounds to benzochlorins and the tin metallation of tetrapyrrolic molecules, all on large scale.

As used herein, the term "tetrapyrrole" or "tetrapyrrolic compound" is intended to encompass a large number of compounds with at least three joined pyrrolic rings having widely differing functionality as described in the literature (for example, see "Porphyrins and Metalloporphyrins" Ed. K. Smith, Elsevier, 1975, N.Y.; "The Porphyrins", Ed. D. Dolphin, Vol. I–V, Academic Press, 1978; and "The Porphyrin Handbook", Ed. K. Kadish, K. M. Smith, R. Guilard, Academic Press, 1999). These compounds contain various and ranging substituents on the β-pyrrole positions or meso-positions of the tetrapyrrolic rings, either symmetrically or asymmetrically substituted on the tetrapyrrolic macrocycle. Simple tetrapyrrolic ring systems include porphyrins, chlorins, iso-bacteriochlorins and bacteriochlorins. Additionally, molecules resembling porphyrins such as corroles, porphodimethenes, phthalocyanines, naphthalocyanines, azoporphyrins, phlorins, texaphyrins, porphyrin "isomers" (such as porphycenes, porphacyanine, homoporphyrins, corrphycenes, vinylogous corroles, vinylogous porphyrins, sapphyrins, pyrhporphyrins, smaragdyrins, isosmaragdyrins, ozaphyrins, pentaphyrins, heteropentaphyrins, orangarins, dehydropentaphyrins, rubyrins, bronzaphyrins, octaphyrins, and the like ) have been developed with a wide range of functionality both at the peripheral positions and at the internal heterocyclic "core" of these molecules. All of these compounds are considered to be within the scope of the term "tetrapyrrole" or "tetrapyrrolic compound" as used herein.

In many of these macrocycles the inner heteroatoms have been replaced by O, S, Se, Te forming new macrocycles with interesting properties. Many of these materials are capable of coordinating metals and will undoubtedly find commercial uses in the fields of medicine and industry and thus are applicable to the inventions set forth in the specification, particularly with regard to formylation, Wittig reactions, demetallation and metallation with tin. Accordingly, there will be a need for highly pure material, especially in pharmaceuticals, which can be made on a large scale.

Examples of the various substituents that can be present on the β-pyrrole or meso-positions of the tetrapyrrolic compounds of the invention include functional groups having a molecular weight less than about 100,000 daltons and can be a biologically active group or organic. Examples are, but are not limited to: (1) hydrogen; (2) halogen, such as fluoro, chloro, iodo and bromo (3) lower alkyl, such as methyl, ethyl, n-propyl, butyl, hexyl, heptyl, octyl, isopropyl, t-butyl, n-pentyl and the like groups; (4) lower alkoxy, such as methoxy, ethoxy, isopropoxy, n-butoxy, t-pentoxy and the like; (5) hydroxy; (6) carboxylic acid or acid salts, such as —CH$_2$COOH, —CH$_2$COONa, —CH$_2$CH$_2$COOH, —CH$_2$CH$_2$COONa, —CH$_2$CH$_2$CH(Br)COOH, —CH$_2$CH$_2$CH(CH$_3$)COOH, —CH$_2$CH(Br)COOH, —CH$_2$CH(CH$_3$)COOH, —CH(Cl)CH$_2$CH(CH$_3$)COOH, —CH$_2$CH$_2$C(CH$_3$)$_2$COOH, —CH$_2$CH$_2$C(CH$_3$)$_2$COOK, —CH$_2$CH$_2$CH$_2$CH$_2$COOH, C(CH$_3$)$_2$COOH, CH(Cl)$_2$COOH and the like; (7) carboxylic acid esters, such as —CH$_2$CH$_2$COOCH$_3$, —CH$_2$CH$_2$COOCH$_2$CH$_3$, —CH$_2$CH(CH$_3$)COOCH$_2$CH$_3$, —CH$_2$CH$_2$CH$_2$COOCH$_2$CH$_2$CH$_3$, —CH₂CH(CH₃)₂COOCH₂CH₃, —CH₂CH₂COOCH₂CH₂OH, —CH₂CH₂COOCH₂CH₂ N(CH₃)₂ and the like; (8) sulfonic acid or acid salts, for example, group I and group II salts, ammonium salts, and organic cation salts such as alkyl and quaternary ammonium salts; (9) sulfonylamides such as —SO₂NH(alkyl), —SO₂N(alkyl)₂, —SO₂NH(alkyl-OH), —SO₂N(alkyl-OH)₂, —SO₂NH(alkyl)-N(alkyl)₂, —SO₂N(alkyl-N(alkyl)₂)₂, SO₂NH(alkyl)-N(alkyl)₃⁺Z⁻) and the like, wherein Z⁻ is a counterion), —SO₂NHCH₂CO₂H, substituted and unsubstituted benzene sulfonamides and sulfonylamides of aminoacids and the like; (10) sulfonic acid esters, such as SO₃(alkyl), SO₃(alkyl-OH), SO₃(alkyl-N(alkyl)₂), SO₃(alkyl-N(alkyl)₃⁺Z⁻) and the like, wherein Z⁻ is a counterion), SO₃CH₂CO₂H, and the like (11) amino, such as unsubstituted or substituted primary amino, methylamino, ethylamino, n-propylamino, isopropylamino, butylamino, sec-butylamino, dimethylamino, trimethylamino, diethylamino, triethylamino, di-n-propylamino, methylethylamino, dimethyl-sec-butylamino, 2-aminoethoxy, ethylenediamino, cyclohexylamino, benzylamino, phenylethylamino, anilino, N-methylanilino, N,N-dimethylanilino, N-methyl-N-ethylanilino, 3,5-dibromo-4-anilino, p-toluidino, diphenylamino, 4,4'-dinitrodiphenylamino and the like; (12) cyano; (13) nitro; or (14) a biologically active group; (15) amides, such as —CH₂CH₂CONHCH₃, —CH₂CH₂CONHCH₂CH₃, —CH₂CH₂CON(CH₃)₂, —CH₂CH₂CON(CH₂CH₃)₂, —CH₂CONHCH₃, —CH₂CONHCH₂CH₃, —CH₂CON(CH₃)₂, —CH₂CON(CH₂CH₃)₂ and amides of amino acids and the like; or (16) iminium salts for example CH═N(CH₃)₂⁺Z⁻; and the like, wherein Z⁻ is a counterion), (17) Boron containing complexes, (18) carbon cage complexes (e.g., C60 and the like), (19) metal cluster complexes, for example derivatives of EDTA, crown ethers, cyclams, cyclens, (20) other porphyrin, chlorin, bacteriochlorin, isobacteriochlorin, azoporphyrin, tetraazoporphyrin, phthalocyanine, naphthalocyanine, texaphyrins, tetrapyrrolic macrocycles or dye class and the like (21) alkynyl, including alkyl, aryl, acid and heteroatom substituted alkynes, and (22) haloalkyl where one or more halogens are substituted onto the alkyl carbon chain, the length of the carbon chain being from C1 to C20; and (23) any other substituent that increases the hydrophilic, amphiphilic or lipophilic nature or stability of the compounds.

The term "biologically active group" as used herein can be any group that selectively promotes the accumulation, elimination, binding rate, or tightness of binding in a particular biological environment. For example, one category of biologically active groups is the substituents derived from sugars, specifically, (1) aldoses such as glyceraldehyde, erythrose, threose, ribose, arabinose, xylose, lyxose, allose, altrose, glucose, mannose, gulose, idose, galactose, and talose; (2) ketoses such as hydroxyacetone, erythrulose, rebulose, xylulose, psicose, fructose, sorbose, and tagatose; (3) pyranoses such as glucopyranose; (4) furanoses such as fructo-furanose; (5) O-acyl derivatives such as penta-O-acetyl-α-glucose; (6) O-methyl derivatives such as methyl α-glucoside, methyl β-glucoside, methyl α-glucopyranoside, and methyl-2,3,4,6-tetra-O-methyl-glucopyranoside; (7) phenylosazones such as glucose phenylosazone; (8) sugar alcohols such as sorbitol, mannitol, glycerol, and myo-inositol; (9) sugar acids such as gluconic acid, glucaric acid and glucuronic acid, δ-gluconolactone, δ-glucuronolactone, ascorbic acid, and dehydroascorbic acid; (10) phosphoric acid esters such as α-glucose 1-phosphoric acid, α-glucose 6-phosphoric acid, α-fructose 1,6-diphosphoric acid, and α-fructose 6-phosphoric acid; (11) deoxy sugars such as 2-deoxy-ribose, rhammose (deoxy-mannose), and fructose (6-deoxy-galactose); (12) amino sugars such as glucosamine and galactosamine; muramic acid and neuraminic acid; (13) disaccharides such as maltose, sucrose and trehalose; (14) trisaccharides such as raffinose (fructose, glucose, galactose) and melezitose (glucose, fructose, glucose); (15) polysaccharides (glycans) such as glucans and mannans; and (16) storage polysaccharides such as α-amylose, amylopectin, dextrins, and dextrans.

Amino acid derivatives are also useful biologically active substituents, such as those derived from valine, leucine, isoleucine, threonine, methionine, phenylalanine, tryptophan, alanine, arginine, aspartic acid, cystine, cysteine, glutamic acid, glycine, histidine, proline, serine, tyrosine, asparagine and glutamine. Also useful are peptides, particularly those known to have affinity for specific receptors, for example, oxytocin, vasopressin, bradykinin, LHRH, thrombin and the like.

Another useful group of biologically active substituents are those derived from nucleosides, for example, ribonucleosides such as adenosine, guanosine, cytidine, and uridine; and 2'-deoxyribonucleosides, such as 2'-deoxyadenosine, 2'-deoxyguanosine, 2'-deoxycytidine, and 2'-deoxythymidine.

Another category of biologically active groups that is particularly useful is any ligand that is specific for a particular biological receptor. The term "ligand specific for a receptor" refers to a moiety that binds a receptor at cell surfaces, and thus contains contours and charge patterns that are complementary to those of the biological receptor. The ligand is not the receptor itself, but a substance complementary to it. It is well understood that a wide variety of cell types have specific receptors designed to bind hormones, growth factors, or neurotransmitters. However, while these embodiments of ligands specific for receptors are known and understood, the phrase "ligand specific for a receptor", as used herein, refers to any substance, natural or synthetic, that binds specifically to a receptor.

Examples of such ligands include: (1) the steroid hormones, such as progesterone, estrogens, androgens, and the adrenal cortical hormones; (2) growth factors, such as epidermal growth factor, nerve growth factor, fibroblast growth factor, and the like; (3) other protein hormones, such as human growth hormone, parathyroid hormone, and the like; (4) neurotransmitters, such as acetylcholine, serotonin, dopamine, and the like; and (5) antibodies. Any analog of these substances that also succeeds in binding to a biological receptor is also included.

Particularly useful examples of substituents tending to increase the amphiphilic nature of the compounds include: (1) short or long chain alcohols, for example, —C₁₂H₂₄—OH where —C₁₂H₂₄ is hydrophobic; (2) fatty acids and their salts, such as the sodium salt of the long-chain fatty acid oleic acid; (3) phosphoglycerides, such as phosphatidic acid, phosphatidyl ethanolamine, phosphatidyl choline, phosphatidyl serine, phosphatidyl inositol, phosphatidyl glycerol, phosphatidyl 3'-O-alanyl glycerol, cardiolipin, or phosphatidal choline; (4) sphingolipids, such as sphingomyelin; and (5) glycolipids, such as glycosyldiacylglycerols, cerebrosides, sulfate esters of cerebrosides or gangliosides. It would be apparent to those skilled in the art what other groups or combinations of the groups described would be suitable to the invention.

Meso-Formylation of Metallo-Tetrapyrroles

It is well established in the literature that many metallated tetrapyrrolic compounds such as Nickel octaethylporphyrin (OEP) and Nickel etioporphyrin I (NiEtio I) undergo electrophilic substitution at the meso position with a Vilsmeier reagent according to schemes 1 and 2 to give compounds (2) and (9). In compounds where all the meso-positions are substituted and free β-pyrrolic positions exist, for example Nickel or Copper tetraphenyl porphyrin derivatives, Vilsmeier formylations occur at the β-pyrrolic positions. Generally on the laboratory scale (grams), the reactions are carried out in hot 1,2-dichloroethane (55–60° C.) and the resulting iminium salt intermediate is hydrolyzed with saturated sodium acetate solution at this elevated temperature. The solution is cooled to room temperature and the organic layer is separated from the aqueous layer. The organic layer is then dried, filtered and evaporated to dryness. The crude residue is best purified by chromatography on silica.

In addition to the mono-meso-formylated products, significant amounts of di-formylated products (Scheme 3) are produced in the reaction in yields between 9–20%. Longer reaction times produce more di-formylated products.

Scheme 3

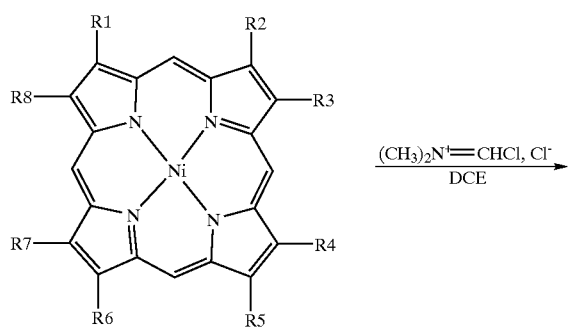

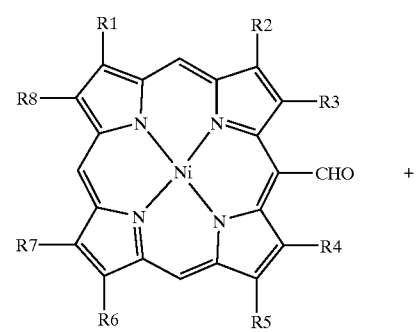

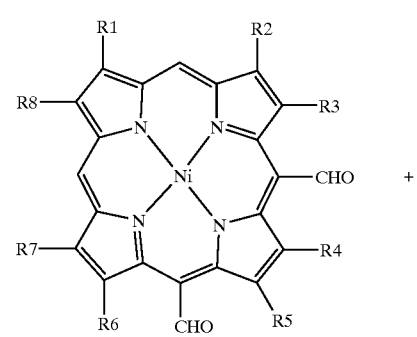

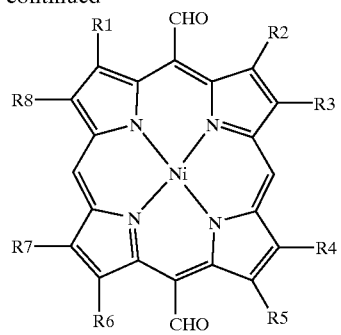

Current literature (K. M. Smith et al., J. Chem. Soc Perk I, p.581, 1982; K. M. Smith et al, Tett. Lett., vol.21, p.3747,1980; G. V. Ponomarev et al, Kimiya Geterotsiklicheskikh Soedinenii, vol.6, p.776, 1979; G. V. Ponomarev et al, Kimiya Geterotsiklicheskikh Soedinenii, vol.6, p.767, 1979; E. Watanabe et al, Tetrahedron, vol.31, p.1385, 1975; K. M. Smith et al, J. Chem. Soc. Perk I, p.439, 1983; G. V. Ponomarev et al, Kimiya Geterotsiklicheskikh Soedinenii, vol.9, p.1215, 1970; A. W. Nichol, J. Chem. Soc. (C) p.903, 1970; G. V. Ponomarev et al, Kimiya Geterotsiklicheskikh Soedinenii, vol.4, p.479, 1984; G. V. Ponomarev et al, Kimiya Geterotsiklicheskikh Soedinenii, vol.11, p.1507, 1982; J. W. Buchler, Leibigs Annalen Chemie, p.43, 1988; A. W. Johnson, J. Chem. Soc., p.4, 1966; H. Brockmann, Leibigs Annalen Chem, vol.148, p.718, 1968; R. Grigg, J. Chem. Soc., p.1789, 1972; R. Grigg, J. Chem. Soc. CCI, p.557, 1979) and patent disclosures (U.S. Pat. Nos. 5,051,415; 5,216,012; 4,877,872; and 5,534,506, the disclosures of which are incorporated herein by reference) in general use chromatography or precipitation from methanol to isolate compounds (2) and (9) in particular from their di-formylated counterparts.

As chromatography on a large scale is an expensive alternative for purification of tetrapyrrolic molecules, the present inventors studied the precipitation of the crude formylated tetrapyrrolic compounds from methanol, ethanol and acetic acid. In this instance, the inventors chose to study compounds (2) and (9). Precipitation of the crude formylated reaction mixture of (2) from dichloromethane/methanol or dichloromethane/ethanol via distillation of the lower boiling solvent was found to be inefficient at removing the di-formylated impurity products from the precipitated product. Approximately the same ratio of diformylated products to mono-formylated products (Table 1 for etioporphyrin series) remained using this procedure.

However, the inventors have found that when alkylcarboxylic acids, such as acetic acid, are used as a precipitating solvent, and the dichloromethane distilled as before, the di-formyl by-products were successfully reduced by approximately 10% per precipitation. This is due to the fact that the di-formylated products possessed greater solubility in the alkylcarboxylic acids than in methanol or ethanol.

The use of alkylcarboxylic acid solvents like acetic acid has several additional advantages. Aqueous residues, which may contain sodium acetate from the hydrolysis step, that have inadvertently found their way into the organic layer during the extraction and separation process are soluble in alkylcarboxylic acids. This is particularly useful in large scale manufacturing where separation of the organic and aqueous phases is sometimes difficult. Additionally, metal free porphyrins, for example etioporphyrin I, which is observed as a minor impurity with Nickel etioporphyrin I (due to incomplete Nickel insertion), has solubility in alkylcarboxylic acids and hence may be reduced in percentage in the final isolated Nickel meso-formyl etioporphyrin I. The fact that many metal-free tetrapyrrolic compounds are soluble in alkylcarboxylic acids enables an efficient means of reducing this impurity in metallated porphyrin derivatives, which in general are less soluble in alkylcarboxylic acids. Additionally, polymeric material produced in the reaction is also soluble in alkylcarboxylic acids.

TABLE 1

HPLC of the crude reaction mixture and precipitations (single)

| | Crude Mixture | Methanol pptn | Ethanol pptn | Acetic acid pptn |
|---|---|---|---|---|
| Ni meso-formyl etioporphyrin | 79.6% | 80% | 76% | 90.1% |
| Ni meso-formyl etioporphyrins | 16% | 15% | 16% | 6.8% |
| Etioporphyrin | 2.4% | 3.0% | 2.6% | 1.6% |
| Ni etioporphyrin | 0.9% | 1.3% | 1.2% | 1.2% |

Yet another major advantage lies with the boiling point of alkylcarboxylic acids. Once the 1,2-dichloromethane has been separated from the aqueous phase, it may be effectively distilled from a mixture of alkylcarboxylic acid/dichloromethane, affecting the precipitation of the desired meso-formyl porphyrin.

Similar observations were made for the formylation of Nickel octaethylporphyrin. The di-formylated Nickel octaethylporphyrin impurities were reduced by levels of 10–15% by a single precipitation from dichloromethane/acetic acid.

Similar results have been obtained for a large number of meso-formylporphyrins, including Nickel meso-formyl etioporphyrin I and II, Copper meso-formyl etioporphyrin I and II, Nickel meso-formyl coproporphyrin I and II tetraalkyl esters, Copper meso-formyl coproporphyrin I and II tetraalkyl esters, Nickel β-formyl tetraphenyl porphyrin, Nickel β-formyl tetrakis((4'-methyl)phenyl))porphyrin, Nickel β-formyl tetrakis((4'-carbomethoxy)phenyl) porphyrin, Copper (II) octaethylporphyrin, Nickel (II) octaethylporphyrin, Copper mesoporphyrin dialkyl ester, and Nickel mesoporphyrin dialkyl ester. It is envisaged that this procedure is generally applicable to the purification of any formylated metallo-tetrapyrrolic compound on a large scale that is not soluble, or has limited solubility in alkylcarboxylic acids. The scope of the invention is not limited to the examples provided herein.

In accordance with another embodiment of the present invention, as embodied and broadly described herein, we have found that the formylation of metallo tetrapyrrolic compounds may be undertaken in a solvent other than 1,2-dichloroethane. As 1,2-dichloroethane is listed as a class 1 solvent by the International Conference on Harmonization (ICH), it would be advantageous on a large-scale to use a less toxic solvent for the formylation of metallo-tetrapyrroles. Toward this goal we used dichloromethane.

Formylation of Nickel etioporphyrin or Nickel octaethylporphyrin with Vilsmeier reagent occurs only slowly at room temperature. In refluxing dichloromethane at atmospheric pressure, the formation of the desired intermediate iminium salt progresses slowly, being complete after approximately 13–24 hours. If the same reaction is undertaken in dichloromethane in a glass lined metal reactor at an elevated temperature such as 35–60° C., preferably 50–60° C., under pressurized conditions, the reaction proceeds smoothly in 3–6 hours. Hence it is possible to replace 1,2-dichloroethane with the less toxic dichloromethane in standard large-scale reactor equipment that is capable of sustaining pressure. Metal glass lined reactor vessels are well suited and designed for such reactions. This procedure is generally applicable to the synthesis of any formylated metallo-tetrapyrrolic compound on a large scale, including but not limited to porphyrins, azoporphyrins, chlorins, isobacteriochlorins and bacteriochlorins. The applicability of this process to other formylated metallo-tetrapyrrolic compounds would be within the knowledge of those skilled in the art.

Wittig Reactions on Meso-Formyl Tetrapyrroles

It is well established in the literature that the formyl group on metallated meso-formyl porphyrins such as meso-formyl Nickel etioporphyrin I (2) and meso-formyl Nickel octaethylporphyrin (9) or on β-formylated porphyrins undergoes Wittig reactions with a large number of Wittig reagents such as, for example, (ethoxycarbonylmethylene) triphenylphosphorane or (methoxycarbonylmethylene)-triphenylphosphorane or the like, to produce the corresponding Wittig addition product porphyrins like meso-acrylate porphyrins (Scheme 4). It should be noted that the term meso-acrylate as used herein is broadly defined as including the following groups: $-CH=CHCO_2Et$; $-CH=CHCO_2Me$; $-CH=CH(ester)$; $-CH=CH(amide)$; $-CH=CHCHO$; $-CH=CHCH(Oalkyl)_2$; $-CH=CHCH(Ocyclicalkyl)_2.$; $-(CH=CH)_n(ester)$ where n=2, 3; $-(CH=CH)_n(CHO)$ where n=2, 3; $-CH=CHCN$; and $-CH=CHCO_2H$. There are a number of "stabilized" Wittig reagents that can be isolated as powders with defined melting points. Such Wittig reagents are useful in the present invention. Also useful are stabilized Wittig reagents that are liquids.

In literature preparations, the Wittig reaction of (ethoxycarbonylmethylene)-triphenylphosphorane or (methoxycarbonylmethylene)triphenyl phosphorane or the like on meso-formyltetrapyrroles is carried out in refluxing xylenes (bp 138–145° C.) under atmospheric conditions (generally overnight) where upon completion of the reaction, the xylene is removed by rotary evaporation and the viscous gummy residue dissolved in dichloromethane. The solution is then chromatographed on silica to remove the desired meso-acrylate porphyrin from the tars and triphenylphosphine oxide produced in the reaction as outlined in the literature (D. P. Arnold, J. Chem. Soc. Perk. I, p.1660, 1978; H. Callott, Bull. Soc. Chim. France. p.3413, 1973; A. R. Morgan et al, J. Org. Chem., vol.51, p.1347, 1986; A. R. Morgan et al, J. Med. Chem., vol.34, p.2126, 1991) and in several patents (U.S. Pat. Nos. 5,051,415 and 5,534,506).

Scheme 4

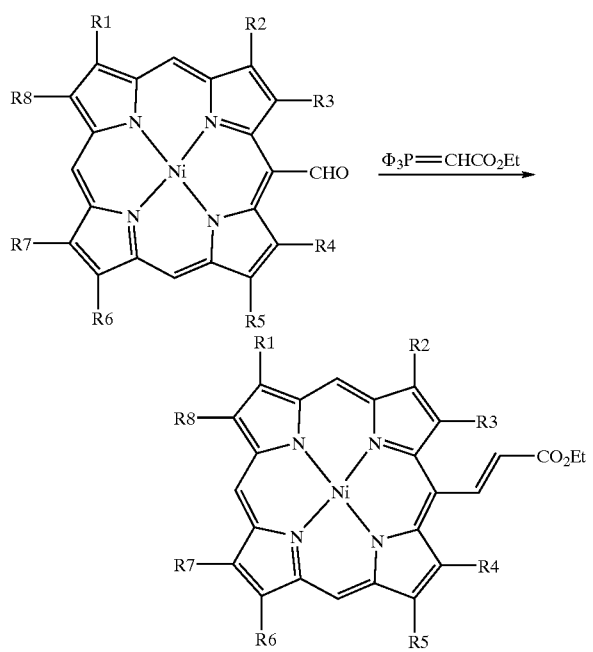

The present inventors have discovered that the reported procedures suffer from a number of disadvantages when going from bench scale (1–5 g) to larger scale. First, it was found that when the reaction was performed in xylene, a large excess of Wittig reagent (typically more than 5 equivalents) was always required to complete the reaction. Even at small scales the reaction was generally slow, requiring at least 15–18 hours of reflux. It was also noted that amounts as high as 10% of Nickel etioporphyrin (or Nickel octaethylporphyrin) were produced during the reaction via deformylation of the starting material. Chromatography of the reaction often yielded the metallated meso-acrylate porphyrin contaminated with triphenyl phosphine oxide due to tailing of the latter through the column. It should be noted that metal-free formyl tetrapyrrolic compounds can also be reacted with Wittig reagents under the same conditions, thereby producing the metal free meso-acrylate compounds directly. These compounds also suffer the disadvantages on purification described above.

As chromatography on a large scale is an expensive alternative for purification of such molecules and because of the problems described, the reaction conditions were modified to best optimize for time, purity, amount of Wittig reagent used, and ease of isolation of the final product. We investigated the reaction in a different solvent, dimethylformamide (DMF), under argon or another inert atmosphere. Under similar conditions as those described by the prior art, it was found that no appreciable amounts of Nickel etioporphyrin I were produced in the reaction. It was also discovered that reducing the volume of DMF in the reaction dramatically decreased the time taken to complete the reaction. In fact, it was found that the reaction could be performed as a melt in which a very small volume of the solvent was present and the temperature was slowly increased to 135° C. over an hour or so with adequate stirring. In this case the reaction was complete in 3–6 hours. Under these conditions, a 2 molar equivalent of phosphorane was used, dramatically reducing the amount of Wittig reagent required from the reported procedure. It was found optimal, however, to have a small amount of solvent (DMF) in the reaction, specifically within about 10% of the weight of the starting meso-formyl tetrapyrrole. The solvent aids in the initial dissolution of the melt and assists in bringing powdered starting material on the sides of the reactor flask into the reaction melt. It is envisaged that this procedure is generally applicable to the Wittig reaction of any formylated tetrapyrrolic compound on a large scale. It is further envisaged that this procedure is particularly applicable to any Wittig reaction where the Wittig reagent is a stable solid or liquid at room temperature. The scope of the invention is not limited to the examples provided herein, but is realized to be generally applicable to metallo or metal free formyl tetrapyrrolic molecules possessing at the β-pyrrole positions, or meso-positions, the functionality described at pages 8–12 herein.

The next challenge was to purify the Nickel meso-acrylate porphyrin from the reaction melt. This was achieved very successfully simply by optionally removing as much of the DMF as possible, allowing the solution to cool, dissolving the crude residue in a solvent and adding a precipitating solvent. Distillation of the solvent with stirring resulted in the precipitation of the desired Nickel meso-acrylate etioporphyrin. The porphyrin can then be filtered directly and optionally washed with the precipitating solvent. The yields from such a procedure are generally about 90% and the purity greater than 98%. Comparable results are obtained with the octaethylporphyrin series and the following meso-formyl tetrapyrrolic compounds: meso-formyl etioporphyrin 1; Nickel meso-formyl etioporphyrin I and II; Copper meso-formyl etioporphyrin I and I; Nickel meso-formyl coproporphyrin I and II; Copper meso-formyl coproporphyrin I and I tetramethyl esters; Nickel β-formyl tetraphenyl porphyrin; Nickel β-formyl tetrakis((4'-methyl)phenyl))porphyrin; Nickel -formyl tetrakis((4'-carbomethoxy)phenyl) porphyrin; and the purification of their acrylate analogues. The precipitation technique described is believed to be applicable to any meso-acrylate (or similar) tetrapyrrolic compound on a large scale that is not soluble, or has limited solubility in alcohols with the functionality described at pages 7–12.

In accordance with the invention, the solvent in the above described precipitation procedure can be halogenated or non-halogenated and is preferably selected from dichloroethane, dichloromethane, ethyl acetate, tetrahydrofuran, acetonitrile, acetone, benzene, toluene, and ethers. The precipitating solvent can also be halogenated or non-halogenated and is preferably selected from acetic acid, propionic acid, methanol, ethanol, 1-propanol, 2-propanol, 1-butanol, hexanes, acetonitrile, ethyl acetate, and iso-octane.

Of particular interest is the composition of the mother liquors of the Wittig reaction on Nickel meso-formyl etioporphyrin 1. They are largely enriched in Nickel etioporphyrin, etioporphyrin, and the Nickel meso-diacrylate etioporphyrins (produced in the reaction from the Nickel di-formyl etioporphyrins). Thus, the alcoholic mother liquors, rich in triphenylphosphine oxide, effectively remove up to 20% of di-formyl etioporphyrin impurities (as their di-acrylate derivatives) carried over in the meso-formyl porphyrin solid of the formylation step, as well as other impurities.

It should be noted that pure di-formyl porphyrins undergo conversion to the di-acrylate porphyrins using the melt conditions described. Additionally, they may be precipitated and purified according to the precipitation technique outlined above. It should be noted that this precipitation technique works especially well for 5, 15-di-acrylate porphyrins as they are generally less soluble in organic solvents. The corresponding 5,10-diacrylate porphyrins are somewhat more soluble and suffer larger losses to the precipitation technique.

Demetallation of Tetrapyrrolic Compounds on a Large Scale

It is well known in the literature that the centrally co-ordinated metal of many metallated porphyrins can be removed by treating the complex with strong acids. Nickel, copper or cobalt porphyrins generally require strong acids, such as sulfuric acid to liberate the metal from the complex. Organic acids, like trifluoroacetic acid, are seldom strong enough to demetallate these complexes, or are very slow at demetallating the complex. Other metals such Zn, In, Ga, Ge, and TI, for example, are rapidly removed from the tetrapyrrolic macrocycles using sulfuric acid, hydrochloric acid, methane sulfonic acid, trifluoroacetic acid, and the like.

In literature preparations, demetallation reactions of nickel or copper porphyrins or other tetrapyrrolic complexes are usually carried out using a large excess of neat sulfuric acid. The acid is either added to the porphyrin or the porphyrin added to the acid. Table 2 gives some literature examples. The solution is then generally added to a neutralizing solution (for example a $NaHCO_3$ solution) and the porphyrin extracted with a solvent and purified. Such procedures are routinely used to demetallate all tetrapyrrolic classes, including porphyrins, chlorins, isobacteriochlorins and bacteriochlorins.

TABLE 2

Literature examples of molar ratios of acid/porphyrin

| Compound/amount | Acid amount (molar equivalents) | Reference |
|---|---|---|
| Meso-acrylate NiOEP(Et ester) (621 mg) | 10 mL $H_2SO_4$ (~92 eq) | U.S. Pat. No. 4,877,872 |
| Meso-acrylate NiOEP(Me ester) (100 mg) | 5 mL $H_2SO_4$ (~306 eq) | D. P. Arnold et al, J. Chem. Soc, 1660, 1978 |
| Meso-acrylate NiEtio(Me ester) (50 mg) | 3 mL $H_2SO_4$ (~334 eq) | D. P. Arnold et al, J. Chem. Soc, 1660, 1978 |
| 5,10-Diacrylate NiOEP(Et ester) (25 mg) | 2 mL $H_2SO_4$ (~579 eq) | A. R. Morgan et al, J. Med. Chem., 34(7), 2126, 1991 |
| 5,15-Diacrylate NiOEP(Et ester) (25 mg) | 2 mL $H_2SO_4$ (~579 eq) | A. R. Morgan et al, J. Med. Chem., 34(7), 2126, 1991 |

We have discovered that the reported procedures suffer from a number of disadvantages when going from bench scale (1 g) to larger scale. In the literature procedures, even on small scale, a large excess of acid is generally required to demetallate the porphyrinic compounds (Table 2). Besides the expense related to using large volumes of acid on large scale, the hazards of handling and neutralizing acid wastes becomes a crucial issue. It would be advantageous to use the minimum amount of acid to effect demetallation so that safety and disposal become more manageable.

A theoretically possible solution to this problem is to "increase the loading" or decrease the equivalents of acid to the starting metal complex. Unfortunately, this approach does not work well with the demetallation of tetrapyrrolic compounds. Regardless of whether the tetrapyrrolic powder is added to the acid or vice versa, severe clumping of the powder occurs. In fact, the powder forms solid clumps that are difficult to disperse under rapid stirring and often stick to the sides of the reactor vessel. This dramatically impacts the amount of demetallation that takes place in the reaction and isolated "demetallated" tetrapyrrolic compound product is invariably contaminated with large amounts of the metallated starting material. The clumping problem makes it virtually impossible to predict when the demetallation reaction is complete.

Another serious limitation in the reported processes involves the neutralization of the acidic solution. The addition of sodium bicarbonate to a highly acidic solution on large scale would be a hazardous undertaking, as a large amount of carbon dioxide is released in the neutralization process (which must be processed accordingly). In addition, extensive frothing and foaming of the solution occurs, which even on a small scale is difficult to control. Total or over neutralization of the solution with NaOH, for example, may cause ester cleavage of tetrapyrroles with ester groups.

We have been able to successfully overcome these problems by utilizing a simple process involving the pre-dissolution of the metallo-tetrapyrrolic compound in a non-water-soluble solvent. Examples of non-water-soluble solvents include 1,2-dichloroethane, 1,1-dichloroethane, dichloromethane, chloroform, benzene, toluene, ether, hexane, xylene, and the like. Initial dissolution of Nickel meso-acrylate porphyrin, for example, in a halogenated solvent like dichloromethane occurs readily. The temperature of the reactor is lowered to approximately 0° C., and the slow addition of an acid with vigorous stirring or agitation results in the acid being dispersed onto the sides of the reaction vessel (as it is not soluble in dichloromethane). The lowering of the temperature avoids any exotherm due to the demetallation reaction. The metallated porphyrin dissolved in the dichloromethane passes over the acid layer and demetallates. It is immediately drawn into the acid layer as its tetraprotonated species. Over a matter of 0.5–1 hour, the metallated porphyrin is continually drawn out of the dichloromethane layer and demetallated.

The completion of the demetallation reaction is easily visualized when the dichloromethane layer is essentially colorless. At this point, water is added to the solution which enables the protonated porphyrin to enter the organic layer (probably as its diprotonated species) and the solution is at least partially neutralized with sodium hydroxide. The organic layer is separated from the at least partially neutralized aqueous layer and reduced in volume by distillation. A precipitating solvent such as, for example, ethanol or methanol is added and the remaining dichloromethane removed by distillation. The precipitating solvent in this instance also acts as a proton sponge, efficiently deprotonating the porphyrin. The thick precipitate is collected by filtration and washed with ethanol. The metal-free meso-acrylate porphyrin isolated is greater than 99% pure. This procedure works equally well with Nickel meso-acrylate octaethylporphyrin.

Using this procedure, it is possible to demetallate a large amount of metallo-tetrapyrrole with very small amounts of acid. Over 240 grams of Nickel meso-acrylate etioporphyrin I (3) can be demetallated with only 250 ml of $H_2SO_4$. Here, approximately 5 equivalents of acid are required to effect demetallation in approximately 1 hour. Identical results are achieved with a large number of different porphyrins. The process is believed to be generally applicable to the demetallation of any metallo-porphyrin, metallo-chlorin, metallo-isobacteriochlorin, metallo-bacteriochlorin, or other metallo-tetrapyrrolic compound that has a co-ordinated metal able to be removed with sulfuric acid. It is also applicable to metallo-tetrapyrroles that are capable of being demetallated with hydrochloric acid or phosphoric acid (for example zinc, indium, gallium, thallium, germanium). Included among the tetrapyrrolic metal complexes suitable for demetallation via this process are those outlined by Johann Walter Buchler in "The Porphyrins", Ed. D. Dolphin, Volume I, Chapter 10, p.389–483, Academic Press, New York, 1978. It is envisaged that such tetrapyrrolic molecules may possess on the β-pyrrolic or meso positions the functionality or combination thereof discussed earlier herein at pages 7–12.

It would be within the general skill and knowledge of those of ordinary skill in the art as to what other functional groups would be amenable to the inventive process or what modifications to the disclosed procedure could be made without departing from the scope of the invention.

Cyclization of Meso-Acrylate Tetrapyrroles to Purpurins

Historically in the literature, the cyclization reaction of meso-acrylate porphyrins to give purpurins has been performed using two different methods. Meso-acrylate octaalkylporphyrins, as shown in Scheme 6, have historically been cyclized to purpurins under acidic conditions, using acetic acid under an inert atmosphere. The cyclization process is slow, requiring typically 24 hours of reflux to attain an equilibrium where approximately 5–10% of starting material is present in the final product. The reaction is also highly sensitive to the presence of oxygen, which causes the formation of other purpurin types that are difficult to remove from the desired product. A significant amount of decomposition also occurs such that the yield of desired product in the presence of oxygen is halved.

octaalkylporphyrins (Scheme 6) do not cyclize using triethylamine or sodium hydroxide as bases.

Scheme 7

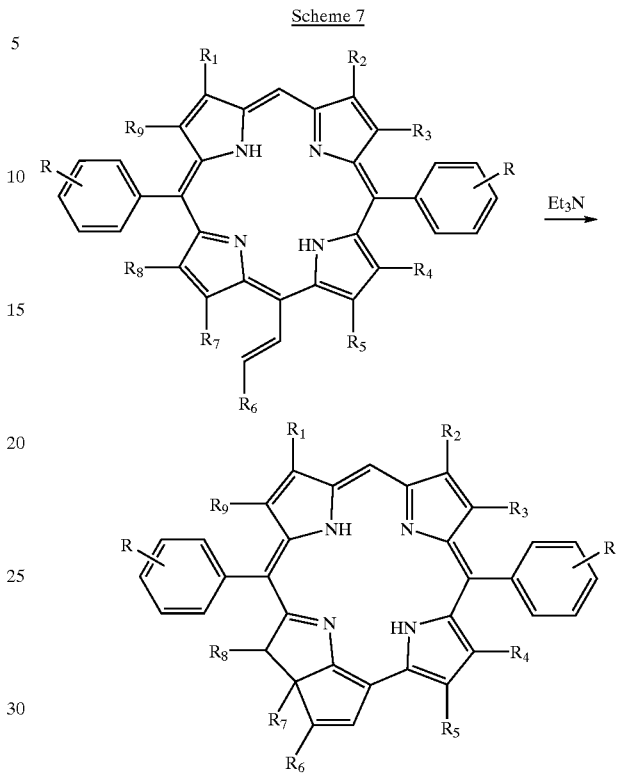

Clearly, the chemistry related to the large scale manufacturing of purpurins from meso-acrylate octaalkylporphyrins needs significant improvement to make it commercially feasible. In addition, meso-acrylate octaalkylporphyrins, such as meso-acrylate etioporphyrin I (or meso-acrylate coproporphyrin I), which bear different alkyl substituents on Scheme 6

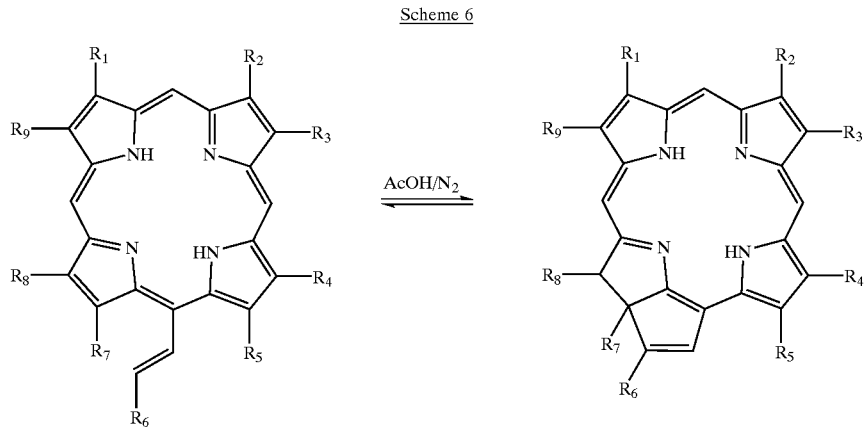

Alternatively, 5,15-Bis aryl 10-acrylate porphyrins (shown in Scheme 7) undergo cyclization to give 5,15-Bis aryl purpurins under basic conditions (Et$_3$N, KSCN or NaOH). Surprisingly, they do not cyclize under acidic conditions. The cyclization reaction is not sensitive to oxygen and there does not appear to be an equilibrium established between starting material and product. Meso-acrylate either side of the meso-acrylate group (scheme 1 at page 4 of the specification) suffer from the formation of cyclization isomers. An example of this is shown in Scheme 1 with the cyclization of meso-acrylate etioporphyrin I (4). Here, cyclization occurs toward an ethyl group on a pyrrole ring to give ethyl etiopurpurin I (5) or toward a methyl group on a pyrrole ring to give methyl etiopurpurin I (6). The product obtained from the acetic acid cyclization route of meso-acrylate etioporphyrin I consists of a mixture of (4), (5) and (6) in a ratio of 3:9:8 and each of (4) and (6) must be separated from (5) for the production of SnET2 (7). See, U.S. Pat. No. 5,051,415. U.S. Pat. No. 5,051,415 does not indicate that (6) is produced in the synthesis, nor does it describe how (4) and (6) are removed from (5).

Over the course of the development of the cyclization process, we investigated base catalysis as an alternative to the acetic acid conditions for cyclizing mono-meso-acrylate tetrapyrrolic compounds to the corresponding purpurin. We investigated a large number of bases and solvents to find the optimal conditions necessary to generate maximal amounts of (5). Table 3 outlines the conditions used. MAE in Table 3 is meso-acrylate etioporphyrin I (4), ET2 is ethyl etiopurpurin (5), and MET2 is methyl etiopurpurin (6).

While we found many of the bases were effective or partially effective at producing purpurin formation, the most effective bases of those we tested were the non-nucleophilic bases 1,5-diazabicyclo[4.3.0]non-5-ene (DBN), 1,5-diazabicyclo[5.4.0]non-5-ene (DBU), tetramethyl guanidine, and pyrrolidine, generally in higher boiling solvents like toluene. The reactions were not sensitive to air (oxygen), and after short reflux times of 4–6 hours, levels of starting material MAE (4) present in the mixture were generally equal to or less than those seen in the long acetic acid reflux cyclization reaction. DBU appeared to give the greatest ratio of ET2 (5):MET2(6):MAE (4), about 72:21:7. In addition to 1,5-diazabicyclo[4.3.0]non-5-ene (DBN), 1,5-diazabicyclo[5.4.0]non-5-ene (DBU), tetramethyl guanidine, and pyrrolidine, the non-nucleophilic base piperidine would also be expected to give similar favorable results.

TABLE 3

Base catalysized Cyclization of meso-acrylate etioporphyrin I (MAE)

| Base | MAE Wt | Solvent | Reflux time | MAE (%) | ET2 (%) | MET2 (%) |
|---|---|---|---|---|---|---|
| DBU | 100 mg | Toluene | 4 hrs | ~7% | 72% | 21% |
| DBN | 100 mg | Toluene | 4 hrs | <10% | 55% | 35% |
| Pyrrolidine | 100 mg | Toluene | 4 hrs | <7% | 71% | 22% |
| Et$_3$N | 100 mg | Toluene | 24 hrs | 100% | NR | NR |
| DMAP | 100 mg | Toluene | 24 hrs | 94% | 4% | 2% |
| Pyridine | 100 mg | neat | 24 hrs | 100% | NR | NR |
| 4-DMAP | 100 mg | Toluene | 24 hrs | 75% | 15% | 5% |
| Tetramethyl guanidine | 100 mg | Toluene | 6 hrs | 7% | 70% | 23% |

DMAP = Dimethylaminopyridine

The challenge then came to separate the two isomeric purpurins ET2 (5) and MET2 (6) without chromatography. Our investigations into the solubility of both compounds led to the discovery that MET2 (6) was much more soluble in acetonitrile and acetone, than was ET2 (5). In fact, we found that ET2 (5) has only limited solubility in hot acetonitrile. Additionally, the starting porphyrin meso-acrylate etioporphyrin I (4) was found to have solubility in acetonitrile and acetone. These discoveries enabled us to develop a simple precipitation process to effectively separate ET2 (5) from MAE (4) and MET2 (6). This process is suitable for use in both traditional acetic acid cyclization reactions as well as the base catalyzed cyclization reactions disclosed herein.

In accordance with the invention, the crude reaction mixture from the base catalyzed or acetic acid cyclization reaction can be evaporated to dryness or near dryness and the residue dissolved in a solvent or mixture of solvents such as dichloromethane. A precipitating solvent such as acetonitrile or acetone can then be introduced, and the solvents(s) removed by distillation. The precipitated product is then filtered rapidly from the warm solution. The mother liquors are rich in small amounts of MAE (4) and mostly MET2 (6). Preferably, the process is repeated until the solid ET2 (5) is sufficiently pure by TLC (0.5% ethylacetate/dichloromethane) or HPLC to proceed to the metallation step and the production of SnET2 (7). In general, three precipitations in this manner has been found to be sufficient to obtain pure product. It would be understood by those skilled in the art that this process may be carried out with a variety of solvents and precipitation solvents in the same or similar manner. Both the solvent and the precipitating solvent can be halogenated or non-halogenated. Preferably, the solvent is dichloromethane, ether, 1,2-dichloroethane, chloroform, toluene, acetone, methanol, ethanol, tetrahydrofuran, ethyl acetate, benzene, or mixtures thereof. The precipitating solvent is preferably methanol, ethanol, 1-propanol, 2-propanol, 1-butanol, t-butanol, acetone, acetonitrile, hexane, heptane, isooctane, cyclohexane, or isopropyl ether.

The isolation of MET2 (6) from the acetonitrile or acetone mother liquors above is a relatively straightforward process. The biggest challenge to overcome lies with the separation of MAE (4) from the MET2 (6). In our tin metallation reactions described earlier, we have observed that free base porphyrins can be metallated effectively at temperatures where the chlorin cannot be metallated (typically 60–80° C.) (see following tin metallation section) in solvents like 1,2-dichloroethane or acetic acid. If the mother liquors of the ET2 precipitation technique described above are evaporated and dissolved in either 1,2-dichloroethane or acetic acid containing a tin salt (preferably SnCl$_2$ predissolved in dimethylformamide) and sodium acetate, any metal-free porphyrins in the crude mixture can be metallated at 30–80° C. with little or no metallation of the chlorin. The crude reaction mixture can then be evaporated to dryness and redissolved in a solvent suitable for chromatography of the material. This method is preferable if the metallation is undertaken in acetic acid or the like.

Alternatively, if the metallation reaction is carried out in 1,2-dichloroethane the solution may be either reduced in volume and chromatographed or directly chromatographed. As tin compounds bind particularly tightly to either silica or alumina, the crude chlorin solution from the metallation reaction can be passed over a small pad of silica or alumina. The tin porphyrins remain on the silica while the chlorin fraction may be eluted from the column under most chromatographic conditions. Such a selective metallation and purification process enables the separation of porphyrinic impurities from chlorins or bacteriochlorins in general. Alternatively, other metals that increase the polarity of the porphyrinic compound on silica or alumina may be used. The metal salts most preferable are those that are readily incorporated into porphyrins at or between 60–80° C. including Sn$^{2+}$ In$^{3+}$, Ga$^{3+}$, Tl$^{3+}$, etc., because these metal salts, when complexed to a tetrapyrrolic molecule, possess an axial ligand that enhances polarity on silica or alumina and enhances the ability to separate the chlorin or bacteriochlorin from the porphyrin impurity. MET2 can then be isolated by chromatography and the resulting MET2 purified by precipitation or crystallization from a solvent such as dichloromethane or a mixture of solvents, and a precipitating solvent in which MET2 is not soluble. In this instance, the solvent can be removed by slow or rotary evaporation resulting in the precipitation of MET2.

The base catalyzed cyclization of meso-acrylate tetrapyrrolic compounds to give purpurins or purpurin type compounds is believed to be applicable to any meso-acrylate (or similar) tetrapyrrolic compound on a large scale. The functionality on the periphery of the meso-acrylate tetrapyrrolic molecule, either at the meso or β-pyrrolic positions may be varied widely as outlined earlier herein at pages 7–12. It would be within the knowledge of those skilled in the art what other functional groups or modifications to this procedure could be made to utilize the invention described.

Large Scale Synthesis of Octaethylbenzochlorin.

A variety of methods have been reported for the synthesis of octaethylbenzochlorin. U.S. Pat. No. 5,552,134 and literature references (Arnold, D. P., Gaete-Holmes, R., Johnson, A. W., Smith, R. P., Williams, G. A., *J. Chem. Soc. Perkin I*, 1660–1670, 1978; Morgan, A. R., Skalkos, D., Maguire, G., Rampersaud, A., Garbo, G., Keck, R., Selman, S. H., *Photochem. Photobiol.* Vol. 55, No.1, 133–136, 1992) outline the synthesis of octaethylbenzochlorin from Nickel meso-(β-formylvinyl)-octaethylporphyrin (14) or from the metal free meso-(β-hydroxymethylvinyl)porphyrin (12) (Scheme 8).

Historically, the formation of octaethylbenzochlorin (OEBC) has been via two routes. First, the metallated meso-acrolein porphyrins (14) and (15) have been cyclized under acidic conditions to give Nickel OEBC (17) (or copper benzochlorin if the copper meso-acrolein porphyrin is used). Demetallation of (17) (or Copper OEBC) is difficult and demetallation with sulfuric acid generally produces OEBC (13) and its sulfonic acid derivative (18) after 3 hours at room temperature.

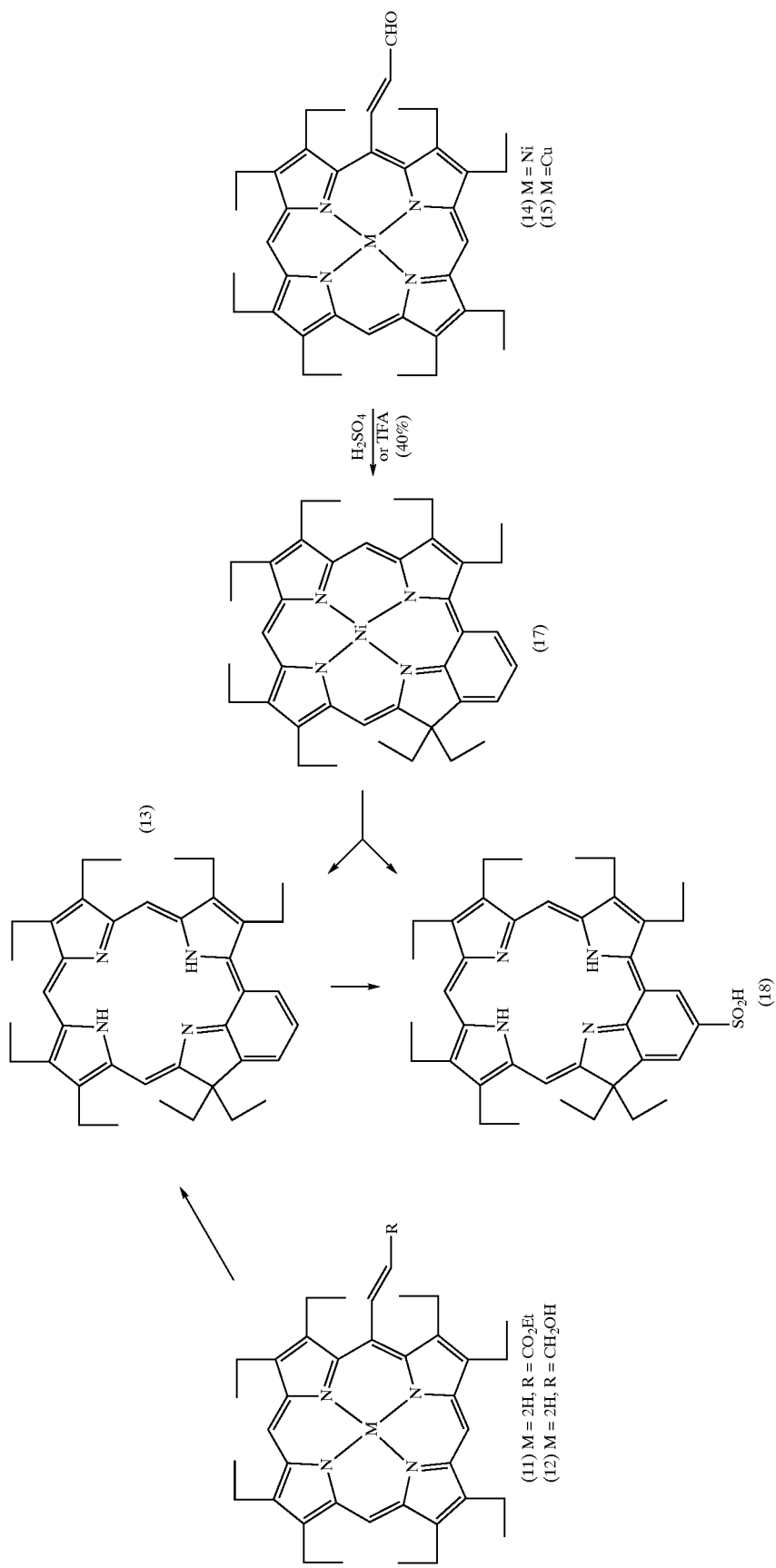

An alternative route outlined by Morgan et al (Morgan, A. R., Skalkos, D., Maguire, G., Rampersaud, A., Garbo, G., Keck, R., Selman, S. H., *Photochem. Photobiol.* Vol. 55, No.1, 133–136, 1992) involves the reduction of the meso-acrylate porphyrin (11) with diisobutyl aluminium hydride in tetrahydrofuran (THF) at low temperature to give the meso-((β-hydroxymethylvinyl)porphyrin (12). This compound is then treated with sulfuric acid for 5 minutes to effect the cyclization and give OEBC (13). Longer reaction times in sulfuric acid leads to significant production of the sulfonated derivative (18).

Neither of these two routes is suitable for manufacturing OEBC on a large scale. The first route gives low yields of the Nickel or copper benzochlorin, generally not greater that 50%, and demetallation of the strongly bound metals (Nickel and Copper) has historically used sulfuric acid. As sulfonation of OEBC occurs rapidly in sulfuric acid (within 3 hours), demetallation of (17) invariably results in the formation of the sulfonated analog, which must be separated by chromatography. The yields thus are disappointing.

The use of diisobutyl aluminium hydride (DIBALH) to reduce the ester functionality of the meso-acrylate porphyrin (11) following Morgan's exact methodology as reported, [(200 mg (11) in THF (100 mL; dry), −78° C./N₂; add DIBALH in THF (200 mL of 1M solution (63 equivalents)), stir 1hr at −78° C.; add water (100 mL) followed by 10% NaOH solution (100 mL) and water (200 mL)] does not work. When we repeated this reported protocol only starting material was isolated. Indeed, the starting material precipitates out of the THF on the addition of water and sodium hydroxide solution. There are no organic layers formed as reported and no appreciable amounts of (12) formed by NMR or TLC. We have observed that the reduction of the ester functionality in THF is an extremely slow reaction, requiring more that 2 days stirring (under Morgan's conditions) to see any appreciable amount of (12). Even under these conditions, the product is mostly (11). Reactions using LiAlH₄ under a variety of conditions give unsatisfactory quantities of (12), which are invariably contaminated with other multiple products by TLC.

An alternative route to the synthesis of NiOEBC has been described by Arnold and co-workers (Scheme 9). In this methodology, the Nickel derivatives (10) or (14) are reduced to (19) with LiAlH₄ or NaBH₄ respectively. Reduction of (10) produces (19) in 36% yield. Treatment of (19) with acid gives Nickel OEBC in 28% yield.

Scheme 9

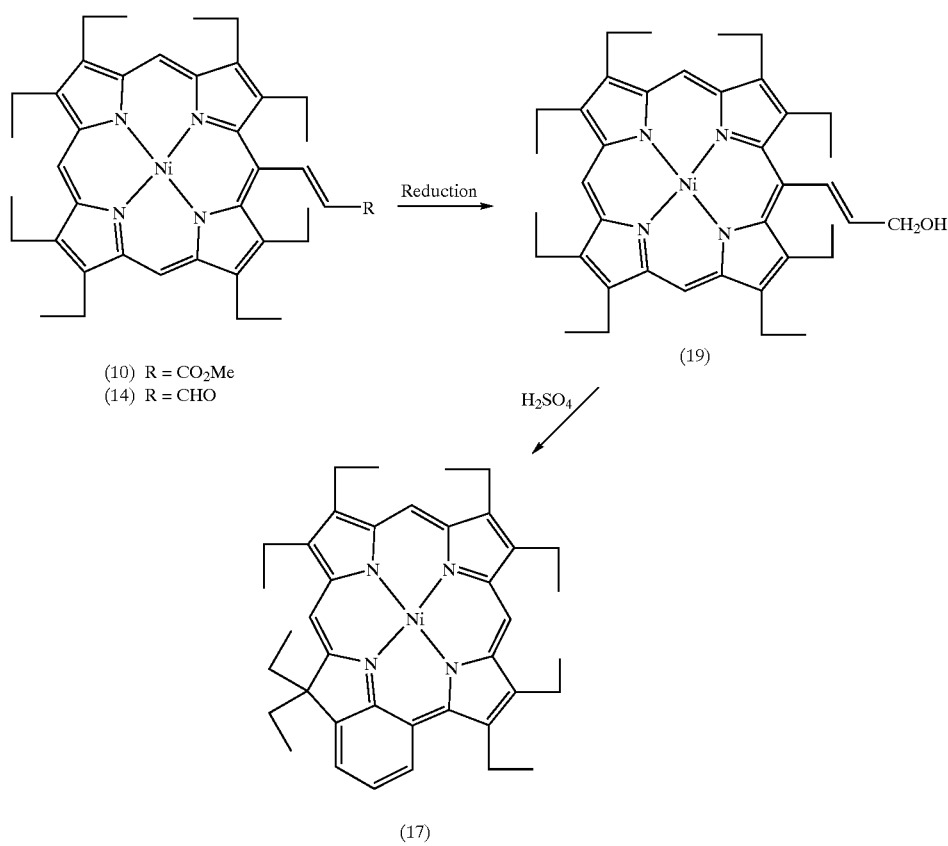

(10) R = CO₂Me
(14) R = CHO (19)

H₂SO₄

(17)

All of the known reported methods for the synthesis of NiOEBC or OEBC directly, suffer from low yields or products that require chromatography to purify. Indeed, the cyclization of the porphyrin precursors in sulfuric acid form sulfonated products like (18). As a result, none of the reported methods is suitable for manufacturing OEBC on a large scale. We have discovered methods that give excellent yields of OEBC from either (11) or NiOEBC, which are described below in detail.

Production of OEBC from Meso-acrylate Octaethylporphyrin (11)

The reduction of the ester group in (11) using DIBALH in THF has been shown to be prohibitively slow for use on a large scale (or even a small scale). We have discovered that the reduction reaction rate is entirely dependent on the solvents utilized in the reaction. If the reduction is undertaken in dichloromethane, using DIBALH in toluene (2.5 equivalents) as the reducing agent, large quantities (>100 g) of (11) are efficiently transformed to (12) in about 4 hours. If THF is used instead of dichloromethane to dissolve (11) and DIBALH in toluene is added to the reaction under the same conditions, the reaction is 1.5 to 2 times slower. Thus, it appears that the reduction of (11) with DIBALH is dependent on the solvent in which the DIBALH is dissolved. The inventors believe that this reaction proceeds most efficiently using a chlorinated solvent such as dichloromethane or 1,2-dichloroethane. The reduction is also dependant on the temperature of the reaction. If the addition of the DIBALH is not closely monitored and the temperature is allowed to rise, significant by-products occur in the reaction. In particular, metallated porphyrins are formed, presumably aluminium porphyrins, at higher temperatures (>−35° C.). It is preferred that the reaction be carried out between about −80° C. and about −35° C.

Literature methods (Morgan et al) have reported isolating the alcohol (12) from the reduction reaction prior to cyclization to give OEBC. We have found that it is not necessary to isolate the alcohol (12) prior to cyclization. During the course of the reduction reaction, small aliquots are taken from the reaction mixture and neutralized with acetic acid/water or ethylacetate and ammonium hydrochloride solution. TLC indicates whether the reaction is complete or not. Once complete, excess DIBALH is quenched with isopropanol/methanol and an acid such as, for example, phosphoric acid (85%) is added. The organic volatiles (dichloromethane and toluene) are removed by distillation (rotoevaporation or other) and the phosphoric acid solution is heated at 60–130° C., preferably at about 100° C. for 3 hours to effect cyclization of (12) to OEBC. The OEBC is conveniently isolated from the phosphoric acid solution by precipitation with water (1.5×the $H_3PO_4$ volume). The OEBC is simply filtered from the acidic aqueous liquors. Any porphyrinic impurities remain protonated and soluble in the acidic aqueous mother liquors. The OEBC solid is then dissolved in dichloromethane and reprecipitated as before (using phosphoric acid/water) or from methanol or ethanol, via the distillation of the dichloromethane. The OEBC obtained in this manner is sufficiently pure to be used further (>97%) and is typically obtained in 70–75% yields. In addition to phosphoric acid, acids that can be preferably used in the above method include, for example, methane sulfonic acid and hydrochloric acid.

If the alcohol (12) needs to be isolated, we have found it convenient to quench the reaction with aqueous ammonia hydrochloride solution. Care must be taken during the quenching process to make sure that the quenching solution is acidic, as it appears that aluminium can be incorporated into the porphyrin. It should be noted also that TFA will not cyclize (12) to OEBC.

OEBC made in this way can be conveniently sulfonated at large scale to produce (18), by dissolving OEBC in sulfuric acid (with or without oleum). After the reaction is complete, (18) is conveniently isolated simply by adding the sulfuric acid to chilled water which precipitates the sulfonated product. It is then filtered and dried in a vacuum oven.

Both the reduction reaction and the acid catalyzed cyclization described in this section are believed to be applicable to any meso-acrylate (or similar) tetrapyrrolic compound on a large scale. The functionality on the periphery of the meso-acrylate tetrapyrrolic molecule, either at the meso or β-pyrrolic positions, can be varied widely as described earlier herein at pages 7–12. It would be within the knowledge of those skilled in the art what other functional groups are susceptible to modification via the reduction conditions or what modifications to this procedure could be made to utilize the invention described.

Demetallation of NIOEBC or CuOEBC Without Sulfonation

The centrally coordinated metal (nickel or copper) of metallated benzochlorin or benzochlorin-type compounds requires strong acid conditions for removal (usually concentrated sulfuric acid) and long reaction times at room temperature (usually overnight). Unfortunately, sulfonation of the benzochlorin occurs readily in this solvent. It is thus very difficult to control the conditions necessary to obtain high yields of demetallated benzochlorins such as OEBC, without concomitant production of the corresponding sulfonated product (18). We have found that the central metal (nickel or copper) of OEBC can be efficiently removed by warming the compound to, for example, 80° C. in methane sulfonic acid. The reaction can be monitored by neutralizing small aliquots of the reaction, dissolving in dichloromethane and evaluating by TLC (30% hexane/dichloromethane). When deemed complete, the reaction can be diluted with ice water (equal volume) and the solid collected by filtration. The solid is washed with methanol or ethanol, redissolved in dichloromethane and precipitated from methanol, to give OEBC in about 80–90% yield, sufficiently pure to undergo further reactions (>97%).

The demetallation reaction described above is believed to be applicable to any benzochlorin or similar tetrapyrrolic compound on a large scale. The functionality on the periphery of the meso-acrylate tetrapyrrolic molecule, either at the meso or β-pyrrolic positions, can be varied widely as described earlier herein at pages 7–12. It would be within the knowledge of those skilled in the art what other functional groups could be used in order to use this demetallation reaction.

Tin Insertion into Tetrapyrrolic Compounds

The formation of metallated porphyrins, chlorins, bacteriochlorins and iso-bacteriochlorins is well established in the literature. Incorporation of metals into these tetrapyrrolic macrocycles can change the photophysical and pharmacokinetic attributes, distribution, metabolism and toxicology of the metallated compound from that of the parent metal-free molecule. In particular, one such metal, tin, has been incorporated into a number of tetrapyrrolic macrocycles that are of interest in medicine or phototherapy. Examples of these compounds include, for example, tin (dichloride) ethyl etiopurpurin I (SnET2; Rostaporfin), tin protoporphyrin (IX) [SnPP(IX)] and tin meso-porphyrin (IX) [SnMPP(IX)] (shown below). SnET2 is currently being evaluated as a photosensitizer in the treatment of age related macular degeneration. SnPP(IX) and SnMPP(IX), as their disodium salts, are currently being evaluated as heme oxygenase inhibitors that decrease the production of bilirubin in infants suffering from hyperbilirubinemia. While there have been few human studies thus far with SnPP(IX) in this role, promising results have been obtained. As the general applicability of photomedicine is realized in disease indications, there will be an increasing need for pure tin tetrapyrrolic macrocyclic compounds.

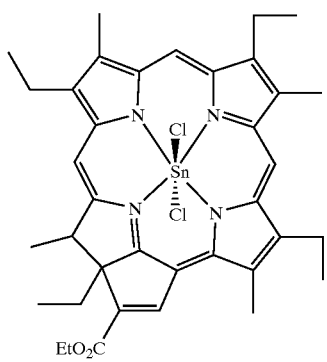

SnET2

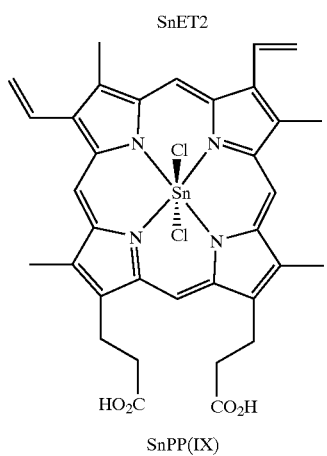

SnPP(IX)

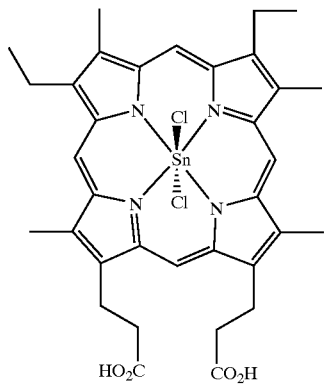

SnMPP(IX)

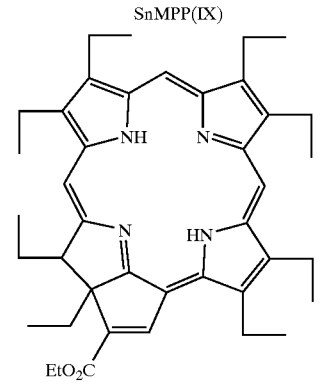

Octaethylpurpurin (32)

The invention described herein relates to the insertion of tin (II) complexes into tetrapyrrolic macrocycles to form tin (IV) metallo-tetrapyrrolic macrocycles. Such compounds, in addition to medicine or phototherapy, may also be useful as molecular wires or as templates for molecular or chiral recognition. In addition, these compounds may also be useful as pharmaceuticals, data storage devices, molecular switches or mimics of biosynthetic processes.

To achieve the advantages in accordance with the purpose of the invention, as embodied and broadly described therein, the inventors have found that a necessary component in the successful formation of highly pure tin (IV) metalloporphyrin complexes, is the abundance of molecular oxygen in the reaction mixture. Indeed, tin insertion into a porphyrin molecule may be achieved at relatively low temperatures provided that an abundance of molecular oxygen is present in the reaction mixture.

Work in our laboratory has explored in detail the chemistry of tin insertion into tetrapyrrolic macrocycles. While there exists many reported methods for inserting tin into tetrapyrrolic macrocycles, we have discovered that even at relatively small scales (grams) the classical methods of inserting tin (II) into tetrapyrrolic macrocycles often lead to the formation of "reduced" tetrapyrrolic side products. Such products are often undesired and are extremely difficult to remove from the desired metallated products as purification of tin tetrapyrroles by chromatography on silica or alumina is extremely difficult. Scheme 10 represents a typical tin insertion reaction into a tetrapyrrolic macrocycle.

Scheme 10

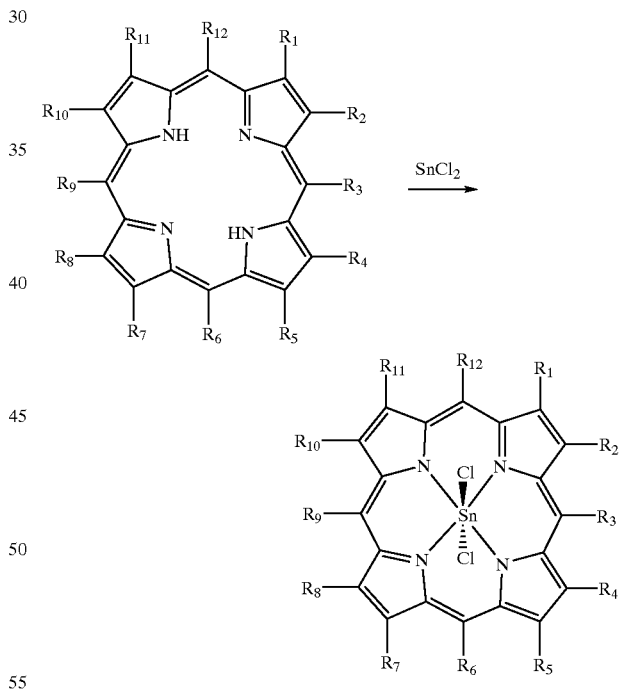

In the metal insertion process, Sn (II) is believed to be inserted into the tetrapyrrolic core as a Sn (II) cation, whereupon rapid oxidation occurs by oxygen or traces of oxidizing impurities to produce the isolated Sn (IV) tetrapyrrolic species. Evidence for the formation of Sn (II) tetrapyrrole complexes has been observed by the isolation of a Sn (II) phthalocyanine. Sn (II) complexes of porphyrins are relatively unknown.

In the metallation reaction, oxidation of Sn (II) to Sn (IV) occurs via oxygen present in the reaction, or other electron rich molecules according to the following equation:

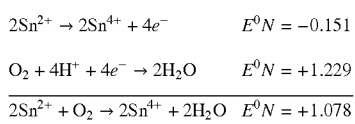

$$2Sn^{2+} + O_2 \rightarrow 2Sn^{4+} + 2H_2O \quad E^0N = +1.078$$

Unfortunately, while the reaction sequence appears relatively straightforward, problems occur when tin metallation is attempted under normal atmospheric conditions in concentrations desirable for large scale manufacturing (or even manufacturing at small scale ~1 g). First, metal insertion is usually undertaken in solvents like glacial acetic acid, dimethylformamide or pyridine at, or close to, their boiling points in the presence of a proton scavenger that absorbs protons of metallation. A particularly preferred proton scavenger is sodium acetate, but others such as salts of other organic acids or amines could also be used effectively. The solvents quickly degas under elevated temperature conditions. In large-scale reactors, the volume between the reaction solvent and the top of the reactor vessel is called headspace. In order to maximize operating efficiency and lower the cost of plant production of the material, headspace is preferably kept to a minimum. Reactions are generally carried out at the highest concentrations of reactants possible in order to maximize efficiency. The combination of solvent degassing, solvent saturated headspace at the reflux temperature, and highly concentrated reaction solutions, leads to less than optimal results in the formation of pure Sn (IV) tetrapyrroles.

The driving force for tin insertion into the macrocycle is the reduction of Sn (II) to Sn (IV). As the metal desires to incorporate into the macrocycle, tetrapyrroles with reducible bonds undergo reductions. Such reductions typically occur on the ring of the macrocycle or at groups on the periphery of the molecule (such as vinyl groups etc). The following are observed examples of unwanted reactions at the porphyrin periphery, which adequately illustrate the observed problem.

Tin metallation of Methyl Pyrropheophorbide (20)

Attempts to insert SnCl₂ into (20) under standard reaction conditions (500 mg of (20) in 70 mL of AcOH, 5 equivalents of NaOAc, 7 equivalents of SnCl₂, followed by reflux) results in the formation of the desired tin metallated pyrropheophorbide (21) and

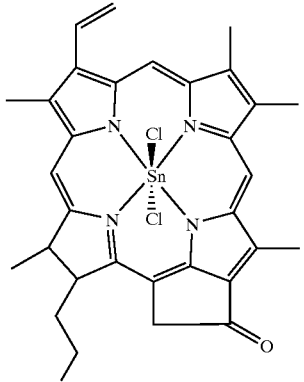

(21)

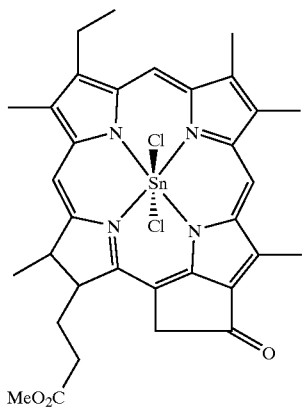

(22)

appreciable amounts (>20%) of (22) in which the peripheral vinyl group has been reduced. If pyridine or dimethylformamide is used as solvent instead of acetic acid, the major product of the reaction is (22).

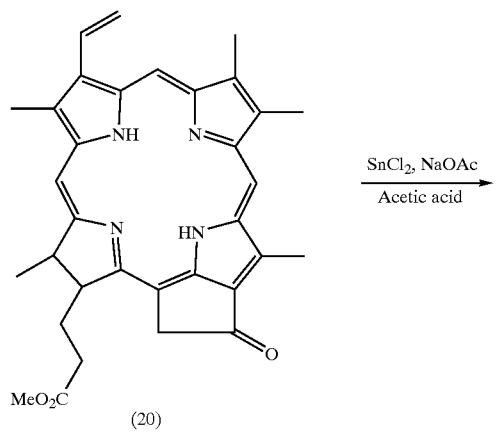

(20)

Tin metallation of Ethyl etiopurpurin (7)

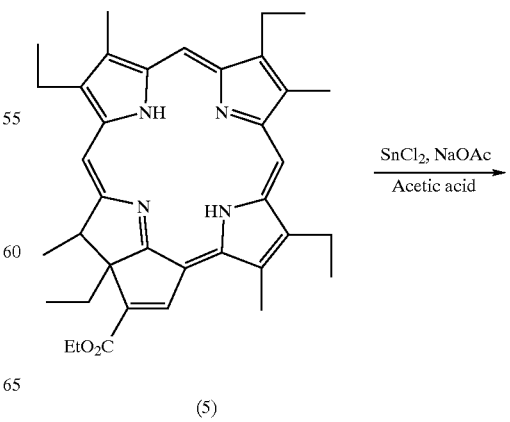

(5)

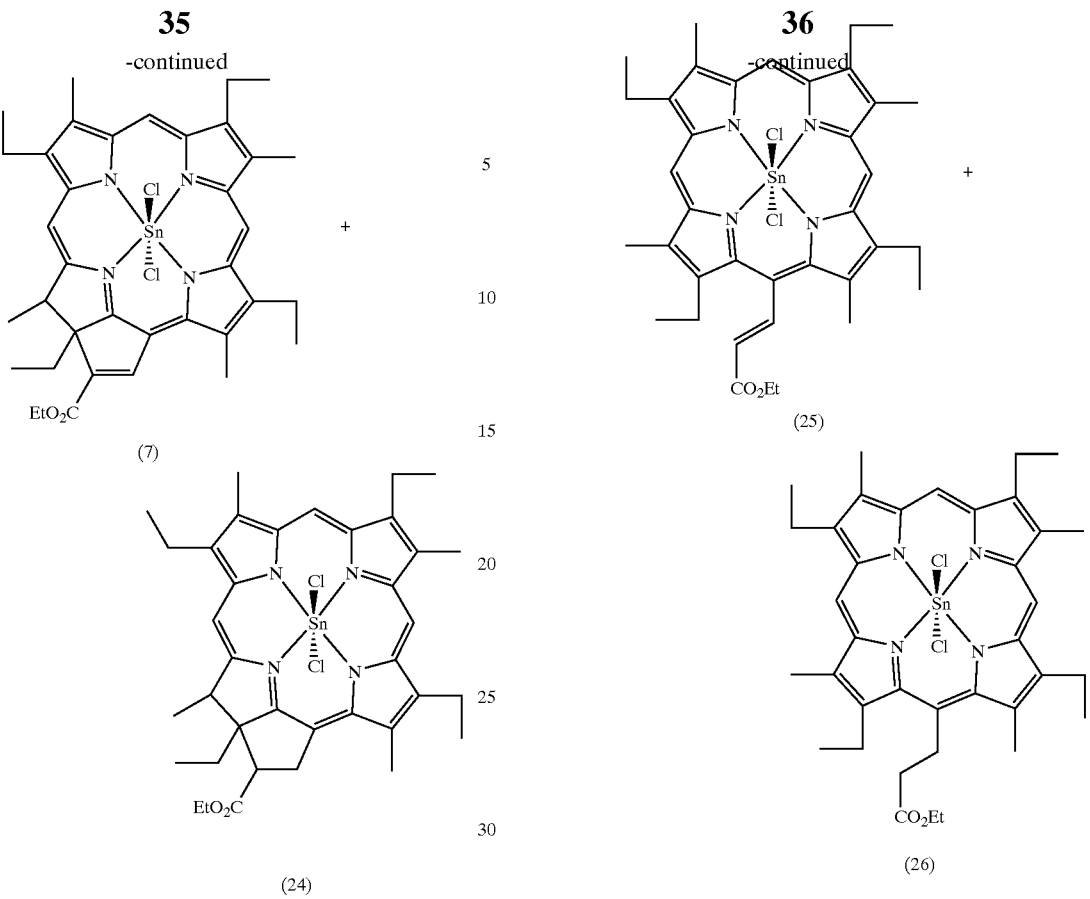

(7)

(24)

(25)

(26)

Attempts to insert SnCl$_2$ into (5) under standard reaction conditions (1 g of (5) in 100 mL of AcOH, 5 equivalents of NaOAc, 7 equivalents of SnCl$_2$, followed by reflux) results in the formation of the desired tin metallated purpurin (SnET2) (7) and appreciable amounts (5–10%) of SnET2H2 (24) in which the peripheral vinyl group of the isocyclic ring has been reduced. If pyridine or dimethylformamide is used as solvent instead of acetic acid, the major product of the reaction is (24). Additionally, the reaction slows substantially if adequate oxygen is not present. We have found that the formation of the impurity (24) is reduced to levels below the limit of quantitation by HPLC if air (or other oxygen containing gas) is bubbled through the solution during the metallation reaction.

Attempts to insert SnCl$_2$ into (4) under standard reaction conditions (1 g of (4) in 100 mL of AcOH, 5 equivalents of NaOAc, 5 equivalents of SnCl$_2$, followed by reflux) results in some formation of the desired tin metallated porphyrin (25), however the major product of the reaction is (26) in which the peripheral vinyl group of the acrylate has been reduced. If pyridine or dimethylformamide is used as the solvent instead of acetic acid, the major product of the reaction is (26). We have found that the meso-acrylate tin porphyrin (25) can only be formed in high purity when dichloroethane is used as a solvent and a vigorous stream of air (or other oxygen containing gas) is bubbled through the solution.

Tin metallation of meso-acrylate etioporphyrin I

Tin metallation of protoporphyrin IX, dimethyl ester (27)

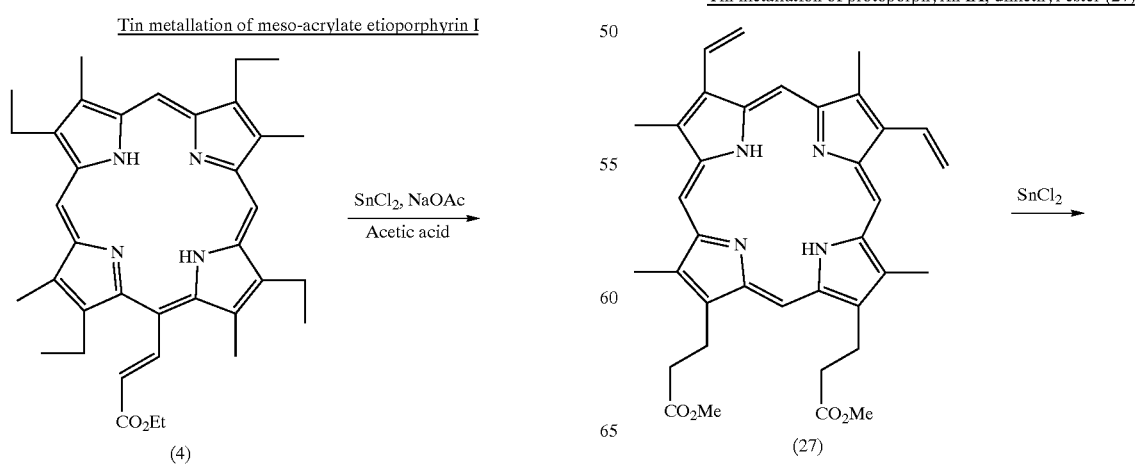

(4) → SnCl$_2$, NaOAc / Acetic acid

(27) → SnCl$_2$

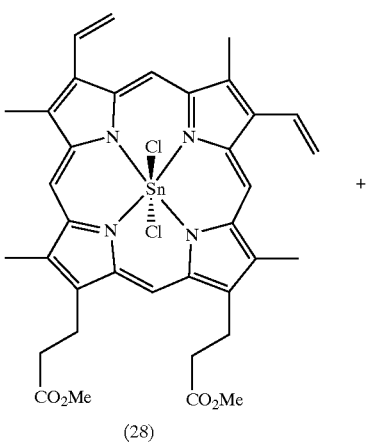

(28)

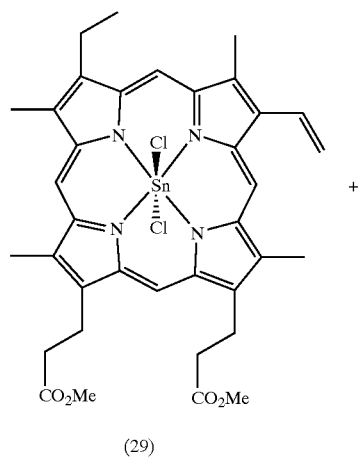

(29)

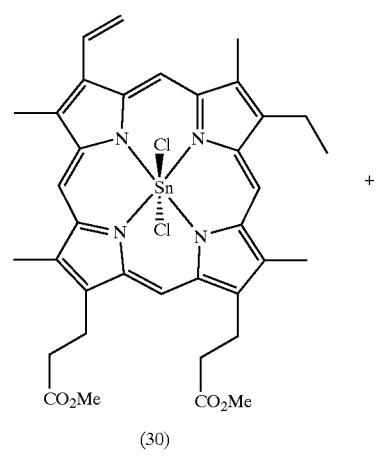

(30)

+

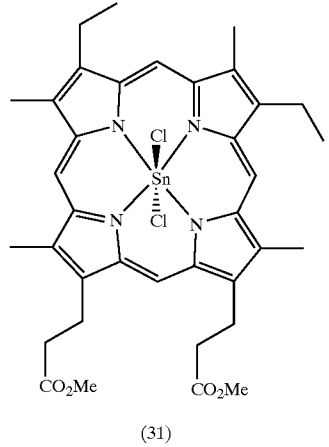

(31)

+

+

Attempts to insert $SnCl_2$ into (27) under standard reaction conditions (1 g of (27) in 100 mL of AcOH, 5 equivalents of NaOAc, 7 equivalent of $SnCl_2$, followed by reflux) results in the formation of the desired tin metallated porphyrin (28). However, by NMR at least 2 major impurities (ranging from 5–15%) are observed. These may be compounds (29) to (31). If pyridine or dimethylformamide is used as the solvent instead of acetic acid, the impurity products increase to 15–25%. The formation of these impurities is limited substantially (to undetectable levels by NMR (<0.4%)) if air (or another oxygen containing gas) is vigorously bubbled through the solution during the metallation reaction. As the solubility of tin salts in a number of common metallation solvents is low, the inventors have also found it advantageous to pre-dissolve the tin salt in a suitable solvent like dimethylformamide, prior to addition to the bulk reaction. This enables rapid incorporation of the tin salt into the macrocycle. Other examples of tin salts that can be used in the invention in addition to $SnCl_2$ include, for example, $Sn(Oac)_2$ and $Sn(acac)_2$. In addition to dimethylformamide, predissolving solvents suitable for use in this process include, for example, acetic acid, propionic acid, or pyrridine.

Additionally, it is recognized in the art that some metallotetrapyrrolic macrocycles such as cadmium tetrapyrrolic will exchange the coordinated metal for a second metal. Such metal exchange reactions are encompassed within the present invention.

In accordance with the invention, as embodied and broadly described herein, the inventors have found that if adequate air is used in the reaction, high purity tin tetrapyrrolic compounds are formed from their corresponding non-metallated tetrapyrrolic compounds. It should be noted that a gas with an oxygen content of at least about 14% by weight is particularly advantageous. In general, many of these compounds crystallize or precipitate from the reaction mixture itself, enabling effective isolation by filtration.

The inventors have found that to obtain highly pure product (>99%), excess salts or impurities can be effectively removed from the reaction mixture on a large scale by precipitation techniques. In the case of tin ethyl etiopurpurin I (7), for example, the crude precipitate of (7) from the metallation reaction can be reprecipitated by first dissolving the purpurin in dichloromethane, adding acetic acid and removing the dichloromethane by distillation. In addition to dichloromethane, other solvents can be used to dissolve the purpurin, such as ether, dichloroethane, chloroform, toluene, or benzene. Other solvents in addition to acetic acid that have been found effective at precipitating the tin purpurin product include, for example, acetone, ethanol, methanol, dimethylformamide and acetonitrile. Of these, acetone and ethanol are preferred. This precipitation technique works similarly with almost all tin tetrapyrrolic compounds on a larger scale (>100 g). In particular, this precipitation technique works effectively with (21), (24), (25), (28) and (31) on scales greater than 50 grams. Of particular note is that the use of high quality solvents with low water contents (especially in the alcohols and acetone) greatly lowers the potential of ligand exchange on the centrally coordinated tin compounds.

It would be within the knowledge of those skilled in the art that other solvents can be used to effectively precipitate the tin tetrapyrrolic complexes. These would include hexanes and the like, ethers and the like, and other alcohols. Examples set forth in the experimental section highlight the general applicability of the precipitation technique. Described above are general procedures for the large scale manufacturing of tetrapyrrolic compounds such as meso-formyl porphyrins, meso-acrylate porphyrins, purpurins, tin metallated tetrapyrroles and benzochlorins. Purification is readily achieved by a series of fractional crystallizations. Additional advantages of the invention will be set forth in the detailed examples that follow, and in part will be obvious from the description supplied or may be learned by practice of the invention. The advantages of the invention can be realized and attained by means of the elements and combinations particularly pointed out in the appended claims. The following examples are included to highlight the advantages over the existing methods and are in no way intended to limit the invention.

EXAMPLES

A) Large scale formulations of metalloporphyrins

Example 1

Preparation of Nickel (II) Meso-Formyl Etioporphyrin 1(2)-Method A 1,2-Dichloroethane (DCE, 8 L) was charged into a 22 L jacketed reaction vessel, followed by Nickel (II) etioporphyrin I (250.0 g, 0.47 mole), and the mixture was stirred slowly to dissolve the solid. During the dissolution, a Vilsmeier reagent [(chloromethylene)dimethylammonium chloride (200.5 g, 1.57 mole)] was added to the Nickel(II) etioporphyrin I solution, followed by DCE (300 mL) to rinse the residual solid from the sides of the vessel. The reaction was warmed to 50–60° C. and held for approximately 5 hours, when the iminium salt formation was determined to be complete by TLC. Subsequently, aqueous sodium acetate (NaOAc·3H$_2$O, 744.0 g, 5.47 moles; H$_2$O, 4L) was added over 46 minutes to hydrolyze the excess Vilsmeier reagent. The mixture was heated to 50–60° C. and held for approximately 45 minutes with rapid stirring, when the hydrolysis was determined to be complete by TLC.

After allowing the two phase system to separate over approximately 14 hours, the organic layer was collected and the aqueous layer was back extracted three times with DCE (2×1000 mL, 1×750 mL). Each back extraction required an additional 1000 mL of purified water to facilitate layer separation. The combined organic layers were then evaporated to dryness at reduced pressure on a rotary evaporator (260–180 mbar, 60–67° C.). DCE (300 mL) was used to rinse the final residue from flasks that contained the original DCE organic layer. This DCE rinse was then added to the rotary evaporation flask. Methylene chloride (CH$_2$Cl$_2$, 3000 mL) was added to the solid residue and the mixture was warmed in a water bath (~35° C.) for about 30 minutes. Acetic acid (1500 mL) was added slowly with swirling to the CH$_2$Cl$_2$ solution and the CH$_2$Cl$_2$ was removed slowly on the rotary evaporator (600–378 mbar, 37–59° C.). The resulting slurry was cooled to ambient temperature over 10 minutes and was then vacuum filtered on a Buchner funnel with hardened qualitative filter paper. The solid was slurried and rinsed in portions with ethanol (2000 mL) and dried in the filter for another 35 minutes. The solid was checked by TLC and then transferred to a vacuum oven and dried to a constant weight at 40–57° C. at a vacuum 29.5–30" Hg for about 21 hours to afford 239.6 g (91.1% yield) of Nickel (II) meso-formyl etioporphyrin I (2).

Example 2

Preparation of Nickel (II) Meso-Formyl Etioporphyrin 1(2)-Method B 1,2-Dichloromethane (DCM, 8 L) was charged into a 10 gal glass lined jacketed metal reactor, followed by Nickel (II) etioporphyrin 1(250.0 g, 0.47 mole), and the mixture was stirred slowly to dissolve the solid. During the dissolution, the Vilsmeier reagent [(chloromethylene) dimethylammonium chloride (200.0 g, 1.56 mole)] was added to the Nicke)(II) etioporphyrin I solution, followed by DCM (300 mL) to rinse the residual solid from the sides of the vessel. The reactor was sealed and warmed to 50–60° C. and held for approximately 5 hours, whereby the reactor was cooled to 10° C. A sample taken from the reactor was analyzed by TLC (DCM) which showed the absence of starting material and iminium salt formation.

Aqueous sodium acetate (NaOAc·3H$_2$O, 744.0 g, 5.47 moles; H$_2$O, 4L) was added over 45 minutes to hydrolyze excess Vilsmeier reagent while maintaining the temperature below 20° C. The reactor was then sealed and the solution vigorously stirred at 35° C. over night. After allowing the two phase system to separate, the organic layer was collected into a second reactor and the aqueous layer in reactor 1 was back extracted three times with DCM (2×1000 mL, 1×750 mL) with the organic layer at each extraction being added to the second reactor. Acetic acid (1500 mL) was added slowly with swirling to the CH$_2$Cl$_2$ solution in reactor 2 and the CH$_2$Cl$_2$ was removed slowly by distillation. The resulting slurry was cooled to ambient temperature and was then line filtered onto a filter disk. Ethanol (2000 mL) was added to the second reactor and the solution rapidly stirred to wash any remaining solid from the sides of the reactor vessel. The solution was again line filtered onto the filter disk containing the product. The product was collected and dried in a vacuum oven to constant weight at 40–60° C. at a vacuum 29.5–30" Hg for about 21 hours to afford 235.0 g (89% yield) of Nickel (II) meso-formyl etioporphyrin I (2).

Example 3

Preparation of Nickel (II) Meso-Formyl Octaethylporphyrin (9)

1,2-Dichloroethane (DCE, 8 L) was charged into a 22 L jacketed reaction vessel, followed by Nickel (II) octaethylporphyrin (250.0 g, 0.42 mole), and the mixture was stirred slowly to dissolve the solid. During the dissolution, Vilsmeier reagent [(chloromethylene)dimethylammonium chloride (200.5 g, 1.57 mole)] was added to the Nicke?(ll) octaethylporphyrin solution, followed by DCE (300 mL) to rinse the residual solid from the sides of the vessel. The reaction was warmed to 50–60° C. and held for approximately 5 hours, when the iminium salt formation was determined to be complete by TLC. Subsequently, aqueous sodium acetate (NaOAc·3H$_2$O, 744.0 g, 5.47 moles; H$_2$O, 4L) was added over 40 minutes to hydrolyze the excess Vilsmeier reagent. The mixture was heated to 50–60° C. and held for approximately 45 minutes with rapid stirring, when the hydrolysis was determined to be complete by TLC.

After allowing the two phase system to separate over approximately 14 hours, the organic layer was collected and the aqueous layer was back extracted three times with DCE (2×1000 mL, 1×750 mL). Each back extraction required an additional 1000 mL of purified water to facilitate layer separation. The combined organic layers were then evaporated to dryness at reduced pressure on a rotary evaporator (260–180 mbar, 60–67° C.). DCE (300 mL) was used to rinse the final residue from flasks that contained the original DCE organic layer. This DCE rinse was then added to the rotary evaporation flask. Methylene chloride (CH$_2$Cl$_2$, 3000 mL) was added to the solid residue and the mixture was warmed in a water bath (~35° C.) for ~30 minutes. Acetic acid (1500 mL) was added slowly with swirling to the CH$_2$Cl$_2$ solution and the CH$_2$Cl$_2$ was removed slowly on the rotary evaporator (600–380 mbar, 40–60° C.). The resulting slurry was cooled to ambient temperature over 10 minutes and was then vacuum filtered on a Buchner funnel with hardened qualitative filter paper. The solid was slurried and rinsed in portions with ethanol (2000 mL) and dried in the filter for another 35 minutes. The solid was checked by TLC and then transferred to a vacuum oven and dried to a constant weight at 40–57° C. at a vacuum 29.5–30" Hg for about 21 hours to afford 240.2 g (91.6% yield) of Nickel (II) meso-formyl octaethylporphyrin (9).

B) Large Scale Wittig Reaction on Meso-Formylporphyrins

Example 4

Preparation of Nickel (II) Meso-Acrvlate Etioporphyrin I (3)

Nickel (II) meso-formyl etioporphyrin I (237.2 g, 0.42 mole), N,N-dimethylformamide (275 mL) and (carbethoxymethylene) triphenylphosphorane (293.4 g, 0.84 mole) were combined in a 3 L round bottom flask and heated at 137–153° C. under an argon blanket for approximately 4 hours. TLC was used to monitor the completion of the reaction. The reaction was cooled to approximately 80° C. and transferred to an evaporation flask with the aid of DMF (300 mL). After the majority of the solvent was removed under vacuum (200–15 mbar) at 74 to 92° C., the residue was heated at >80° C. under vacuum (<70 mbar) for an additional 28 minutes. To the resulting solid, which was cooled in an ambient water bath, methylene chloride (1750 mL) was added and the mixture was warmed to 35–40° C. for 35 minutes to dissolve the solid. Then ethanol (2000 mL) was added with swirling and the methylene chloride was slowly removed under vacuum (700–400 mbar, 40–49° C.) to precipitate the product. The slurry was cooled to ambient temperature over 7 minutes and the product collected by vacuum filtration on a Buchner funnel with hardened qualitative filter paper, slurried and rinsed in portions with ethanol (2500 mL) and dried until the solid caked. The solid was checked by TLC and then transferred to a vacuum oven and dried at 40–55° C., 28.5–30" Hg for approximately 21 hours to a constant weight to afford 239.2 g (89.7% yield) of Nickel (II) meso-acrylate etioporphyrin I (3).

Example 5

Preparation of Nickel (II) Meso-Acrylate Octaethylporphyrin (10)

Nickel (II) meso-formyl octaethylporphyrin (237.2 g, 0.40 mole), N,N-dimethylformamide (275 mL) and (carbethoxymethylene) triphenylphosphorane (278.7 g, 0.80 mole) were combined in a 3 L round bottom flask and heated at 137–153° C. under an argon blanket for approximately 4 hours. TLC was used to monitor the completion of the reaction. The reaction was cooled to approximately 80° C. and transferred to an evaporation flask with the aid of DMF (300 mL). After the majority of the solvent was removed under vacuum (200–15 mbar) at 74 to 92° C., the residue was heated at $\geq$80° C. under vacuum ($\leq$70 mbar) for an additional 25 minutes. To the resulting solid, which was cooled in an ambient water bath, methylene chloride (1750 mL) was added and the mixture was warmed to 35–40° C. for 35 minutes to dissolve the solid. Then ethanol (2000 mL) was added with swirling and the methylene chloride was slowly removed under vacuum (700–400 mbar, 40–49° C.) to precipitate the product. The slurry was cooled to ambient temperature over 10 minutes and the product collected by vacuum filtration on a Buchner funnel with hardened qualitative filter paper, slurried and rinsed in portions with ethanol (2500 mL) and dried until the solid caked. The solid was checked by TLC and then transferred to a vacuum oven and dried at 40–55° C., 28.5–30" Hg for approximately 21 hours to a constant weight to afford 240.2 g (90% yield) of Nickel (II) meso-acrylate octaethylporphyrin (10).

Example 6

Preparation of Meso-Acrylate Etioporphyrin 1(4)

A solution of methylene chloride (3250 mL) and Nickel (II) mesoacrylate etioporphyrin I (237.1 g, 0.37 mole), plus an additional 250 mL of CH$_2$Cl$_2$ to rinse the sides of the vessel, was cooled to 0° C. in a jacketed 22 L reaction vessel. Then, concentrated H$_2$SO$_4$ (250 mL, ~4.5 moles) was added slowly with vigorous stirring, followed by 300 mL of CH$_2$Cl$_2$ to rinse the sides of the vessel. The stirring was continued for a total of 33 minutes, and then cold water (5 L) was slowly added to the reaction vessel with moderate stirring, maintaining the temperature at $\leq$11° C. The reaction was cooled to 2° C., and then aqueous NaOH (NaOH, 230.0 g, 5.75 mole; H$_2$O, 2000 mL) was added slowly, maintaining the temperature at $\leq$10° C.

The layers were separated and the aqueous layer was back extracted twice with CH$_2$Cl$_2$ (2×1000 mL). The organic layers were combined and concentrated under vacuum (700–660 mbar, 35–40° C.) until approximately 1500 mL of CH$_2$Cl$_2$ remained. During the solvent removal, CH$_2$Cl$_2$ (300 mL) was used to rinse the organic layer collection flasks and was added to the CH$_2$Cl$_2$ solution. Ethanol (1700 mL) was then added with swirling, and the remaining CH$_2$Cl$_2$ was removed under vacuum (600–335 mbar, 42–50° C.) to precipitate the product. The slurry was cooled over approximately 1 hour and the product was vacuum filtered on a Buchner funnel with hardened qualitative filter paper. The solid was slurried and rinsed in portions with ethanol (2000 mL), and then dried under vacuum until the solid caked. The product was checked by TLC and then dried for approximately 27 hours under vacuum (29–29.5" Hg) at an end temperature of 56° C. to a constant weight, affording 206.6 g (95.7% yield) of meso-acrylate etioporphyrin I (4).

Example 7

Preparation of Meso-Acrylate Octaethylporphyrin I (11)

A solution of methylene chloride (3250 mL) and Nickel (II) meso-acrylate octaethylporphyrin (240 g, 0.35 mole), plus an additional 250 mL of CH$_2$Cl$_2$ to rinse the sides of the vessel, was cooled to 0° C. in a jacketed 22 L reaction vessel. Then, concentrated H$_2$SO$_4$ (250 mL, ~4.5 moles) was added slowly with vigorous stirring, followed by 300 mL of CH$_2$Cl$_2$ to rinse the sides of the vessel. The stirring was continued for a total of 35 minutes, and then cold water (5 L) was slowly added to the reaction vessel with moderate stirring, maintaining the temperature at ≦10° C. The reaction was cooled to 0° C., and then aqueous NaOH (NaOH, 230.0 g, 5.75 mole; H$_2$O, 2000 mL) was added slowly, maintaining the temperature at ≦10° C.

The layers were separated and the aqueous layer was back extracted twice with CH$_2$Cl$_2$ (2×1000 mL). The organic layers were combined and concentrated under vacuum (700–660 mbar, 35–40° C.) until approximately 1500 mL of CH$_2$Cl$_2$ remained. During the solvent removal, CH$_2$Cl$_2$ (300 mL) was used to rinse the organic layer collection flasks and was added to the CH$_2$Cl$_2$ solution. Ethanol (1700 mL) was then added with swirling, and the remaining CH$_2$Cl$_2$ was removed under vacuum (600–335 mbar, 40–50° C.) to precipitate the product. The slurry was cooled over approximately 1 hour and the product was vacuum filtered on a Buchner funnel with hardened qualitative filter paper. The solid was slurried and rinsed in portions with ethanol (2000 mL), and then dried under vacuum until the solid caked. The product was checked by TLC and then dried for approximately 27 hours under vacuum (29–29.5" Hg) at an end temperature of 60° C. to a constant weight, affording 211.8. g (95.7% yield) of meso-acrylate octaethylporphyrin (11).

Example 8

Preparation of Ethyl Etiopurpurin 1(5)-Method A

Meso-acrylate etioporphyrin I (4) (204.7 g, 0.36 mole), toluene (3750 mL) and 1,8-diazabicyclo [5.4.0] undec-7-ene (DBU, 20 mL, 0.13 mole) were combined in a 12 L round bottom reaction vessel and purged with argon for 21 minutes, brought to reflux and stirred for approximately 5 hours under an argon atmosphere. TLC was used to monitor the completion of the reaction. The reaction was cooled to ambient temperature, transferred to an evaporation flask with the aid of additional toluene (210 mL) and the solvent was removed under vacuum (98–30 mbar, 60–70° C.).

Methylene chloride (4000 mL) was added to the solid and the mixture was warmed with swirling at 35–41° C. for 35 minutes. Acetonitrile (2500 mL) was added in portions with swirling as the CH$_2$Cl$_2$ was removed at reduced pressure (700–408 mbar, 45–55° C.). The slurry was vacuum filtered while still warm on a Buchner funnel with hardened qualitative filter paper and the solid was slurried and rinsed in portions with acetonitrile (1750 mL), and then dried until the solid caked. The solid was transferred to an evaporation flask with CH$_2$Cl (4000 mL) and the mixture was warmed with swirling at 35–45° C. for 30 minutes. Acetonitrile (2500 mL) was added in portions with swirling as the CH$_2$Cl was removed at reduced pressure (695–460 mbar, 45–55° C.). The warm slurry was vacuum filtered on a Buchner funnel with hardened qualitative filter paper and the solid was slurried and rinsed in portions with acetonitrile (1500 mL), then dried until the solid caked. The solid was transferred to an evaporation flask with CH$_2$Cl (4000 mL) and the mixture was warmed with swirling at 40–44° C. for 30 minutes. Acetonitrile (2500 mL) was added in portions with swirling as the CH$_2$Cl was removed at reduced pressure (700–466 mbar, 45–55° C.). The warm slurry was vacuum filtered on a Buchner funnel with hardened qualitative filter paper and the solid was slurried and rinsed in portions with acetonitrile (1500 mL), then dried until the solid caked. The solid was analyzed by TLC to determine the purity and then dried under vacuum (30" Hg) at 52–57° C. for approximately 21 hours to a constant weight to yield 130.3 g (63.7% yield) of ethyl etiopurpurin I (5).

Example 9

Preparation of Ethyl Etiopurpurin I (5)-Method B

Meso-acrylate etioporphyrin I (4) (205.0 g, 0.36 mole), toluene (3750 mL) and 1,8-diazabicyclo [5.3.0] undec-5-ene (DBN, 20 mL, 0.16 mole) were combined in a 12 L round bottom reaction vessel and purged with argon for 20 minutes, brought to reflux and stirred for approximately 5 hours under an argon atmosphere. TLC was used to monitor the completion of the reaction. The reaction was cooled to ambient temperature, transferred to an evaporation flask with the aid of additional toluene (210 mL) and the solvent was removed under vacuum (98–30 mbar, 60–70° C.).

Methylene chloride (4000 mL) was added to the solid and the mixture was warmed with swirling at 35–40° C. for 35 minutes. Acetonitrile (2500 mL) was added in portions with swirling as the CH$_2$Cl$_2$ was removed at reduced pressure (700–400 mbar, 45–55° C.). The slurry was vacuum filtered while still warm on a Buchner funnel with hardened qualitative filter paper and the solid was slurried and rinsed in portions with acetonitrile (1750 mL), and then dried until the solid caked. The solid was transferred to an evaporation flask with CH$_2$Cl$_2$ (4000 mL) and the mixture was warmed with swirling at 35–45° C. for 30 minutes. Acetonitrile (2500 mL) was added in portions with swirling as the CH$_2$Cl$_2$ was removed at reduced pressure (700–460 mbar, 45–55° C.). The warm slurry was vacuum filtered on a Buchner funnel with hardened qualitative filter paper and the solid was slurried and rinsed in portions with acetonitrile (1500 mL), then dried until the solid caked. The solid was transferred to an evaporation flask with CH$_2$Cl$_2$ (4000 mL) and the mixture was warmed with swirling at 40–42° C. for 30 minutes. Acetonitrile (2500 mL) was added in portions with swirling as the CH$_2$Cl$_2$ was removed at reduced pressure (700–460 mbar, 45–55° C.). The warm slurry was vacuum filtered on a Buchner funnel with hardened qualitative filter paper and the solid was slurried and rinsed in portions with acetonitrile (1500 mL), then dried until the solid caked. The solid was analyzed by TLC to determine the purity and then dried under vacuum (30" Hg) at 52–59° C. for approximately 21 hours to a constant weight to yield 125.4 g (61.2% yield) of ethyl etiopurpurin I (5).

Example 10

Preparation of Ethyl etiopurpurin I (5)-Method C

Meso-acrylate etioporphyrin I (4) (205.1 g, 0.36 mole) and acetic acid (3750 mL) were combined in a 12 L round bottom reaction vessel and purged with argon for 22 minutes, brought to reflux and stirred for approximately 24 hours under an argon atmosphere. The reaction was cooled to ambient temperature, transferred to an evaporation flask with the aid of dichloromethane (200 mL) and the solvents were removed under vacuum. Ethanol (500 mL) was added and removed by rotoevaporation. Methylene chloride (4000 mL) was added to the solid and the mixture was warmed with swirling at 35–40° C. for 30 minutes. Acetonitrile (2500 mL) was added in portions with swirling as the $CH_2Cl_2$ was removed at reduced pressure (700–400 mbar, 45–55° C.). The slurry was vacuum filtered while still warm on a Buchner funnel with hardened qualitative filter paper and the solid was slurried and rinsed in portions with acetonitrile (1750 mL), and then dried until the solid caked. The solid was transferred to an evaporation flask with $CH_2Cl_2$ (4000 mL) and the mixture was warmed with swirling at 35–45° C. for 30 minutes. Acetonitrile (2500 mL) was added in portions with swirling as the $CH_2Cl_2$ was removed at reduced pressure (700–460 mbar, 45–55° C.). The warm slurry was vacuum filtered on a Buchner funnel with hardened qualitative filter paper and the solid was slurried and rinsed in portions with acetonitrile (1500 mL), then dried until the solid caked. The solid was transferred to an evaporation flask with $CH_2Cl_2$ (4000 mL) and the mixture was warmed with swirling at 36–40° C. for 30 minutes. Acetonitrile (2500 mL) was added in portions with swirling as the $CH_2Cl_2$ was removed at reduced pressure (700–460 mbar, 45–55° C.). The warm slurry was vacuum filtered on a Buchner funnel with hardened qualitative filter paper and the solid was slurried and rinsed in portions with acetonitrile (1500 mL), then dried until the solid caked. The solid was analyzed by TLC to determine the purity and then dried under vacuum (30" Hg) at 50–57° C. for approximately 21 hours to a constant weight to yield 102.2 g (50% yield) of ethyl etiopurpurin I (5).

Example 11

Preparation of Ethyl etiopurpurin I (5)-Method D

Meso-acrylate etioporphyrin I (4) (205.0 g, 0.36 mole), toluene (3750 mL) and 1,8-diazabicyclo[5.4.0]undec-7-ene (DBU, 20 mL, 0.13 mole) were combined in a 12 L round bottom reaction vessel and purged with argon for 21 minutes, brought to reflux and stirred for approximately 5 hours under an argon atmosphere. TLC was used to monitor the completion of the reaction. The reaction was cooled to ambient temperature, transferred to an evaporation flask with the aid of additional toluene (210 mL) and the solvent was removed under vacuum (98–30 mbar, 60–70° C.).

Methylene chloride (4000 mL) was added to the solid and the mixture was warmed with swirling at 35–41° C. for 35 minutes. Acetone (2000 mL) was added in portions with swirling as the $CH_2Cl_2$ was removed at reduced pressure (700–690 mbar, 45–50° C.). The slurry was vacuum filtered on a Buchner funnel with hardened qualitative filter paper and the solid was slurried and rinsed in portions with acetonitrile (1750 mL), and then dried until the solid caked. The solid was transferred to an evaporation flask with $CH_2Cl_2$ (4000 mL) and the mixture was warmed with swirling at 35–45° C. for 30 minutes. Acetone (2000 mL) was added in portions with swirling as the $CH_2Cl_2$ was removed at reduced pressure (700–690 mbar, 45–50° C.). The slurry was vacuum filtered on a Buchner funnel with hardened qualitative filter paper and the solid was slurried and rinsed in portions with acetonitrile (1500 mL), then dried until the solid caked. The solid was analyzed by TLC to determine the purity (a third precipitation may be undertaken) and then dried under vacuum (30" g) at 52–60° C. for approximately 21 hours to a constant weight to yield 122.3 g (59% yield) of ethyl etiopurpurin I (5).

Example 12

Preparation of Tin Dichloride Ethyl Etiopurpurin (7) (Method A)

Ethyl etiopurpurin I (128.0 g, 0.22 mole), anhydrous sodium acetate (45.5 g, 0.55 mole) and glacial acetic acid (7500 mL) were combined in a 12 L round bottom reaction vessel and purged with compressed air for 36 minutes via a wide bore glass bubbler. Then anhydrous tin chloride (231.6 g, 1.22 mole), predissolved with heat in N,N-dimethylformamide (139 mL), was added to the solution and the reaction mixture was heated to 105° C. with stirring and constant purging with air, for approximately 3.5 hours. Upon completion of the reaction by UV\Vis and TLC, the reaction was cooled to 75° C. with stirring at which point stirring was stopped and the solution was allowed to cool to ambient temperature. The solid crystalline product was vacuum filtered on a Buchner funnel with hardened qualitative filter paper, and rinsed in portions with acetic acid (1600 mL), and dried until the solid caked. The solid was then transferred to another filter funnel containing hardened qualitative filter paper, and $CH_2Cl_2$ (5000 mL, in portions) was used to dissolve the solid in the filter funnel and the $CH_2Cl_2$ solution was vacuum filtered through the funnel. The $CH_2Cl_2$ solution was transferred to an evaporation flask with the aid of 300 mL of additional $CH_2Cl_2$ and the solution was concentrated to approximately 3500 mL under vacuum (695 mbar, 41–42° C.). Acetic acid (1250 mL) was added with swirling and the $CH_2Cl_2$ was removed under vacuum (695–390 mbar, 42–52° C.). The resulting slurry was cooled to ambient temperature and vacuum filtered on a Buchner funnel with hardened qualitative filter paper. The solid was slurried and rinsed in portions with acetic acid (1000 mL) and then rinsed with 500 mL of acetone. The product was then dried in a vacuum oven (30" Hg) at 48–62° C. for approximately 54.5 hours to a constant weight. The solid was transferred to an evaporation flask with $CH_2Cl_2$ (4500 mL) and the mixture was warmed at 35–42° C. for 30 minutes. Acetone (2540 mL) was added with swirling as the $CH_2Cl_2$ was removed under vacuum (700–697 mbar, 42–50° C.). The resulting slurry was cooled to ambient temperature over 19 minutes.

The product was collected by vacuum filtration on a Buchner funnel with hardened qualitative filter paper, slurried and rinsed in portions with acetone (1010 mL), and dried in a vacuum oven (30" Hg) at 56–58° C. for 28.5 hours to a constant weight. The solid was then dried an additional 23 hours to give 149.0 g (90.8% yield) of tin dichloride ethyl etiopurpurin (7) (purity >99% by HPLC).

Example 13

Preparation of Tin Dichloride Ethyl Etiopurpurin (7) (Method B)

Ethyl etiopurpurin I (128.0 g, 0.22 mole), anhydrous sodium acetate (45.5 g, 0.55 mole) and glacial acetic acid (7500 mL) were combined in a 12 L round bottom reaction vessel and purged with compressed air for 30 minutes via a wide bore glass bubbler. Then anhydrous tin chloride (231.6 g, 1.22 mole), predissolved with heat in N,N-dimethylformamide (139 mL), was added to the solution and the reaction mixture was heated to 105° C. with stirring and constant purging with air, for approximately 3.5 hours. Upon completion of the reaction by UV/Vis and TLC, the reaction was cooled to 75° C. with stirring at which point stirring was stopped and the solution was allowed to cool to ambient temperature for approximately 16.5 hours. The solid crystalline product was vacuum filtered on a Buchner funnel with hardened qualitative filter paper, and rinsed in portions with acetic acid (1600 mL), and dried until the solid caked. The solid was then transferred to another filter funnel containing hardened qualitative filter paper, and $CH_2Cl_2$ (5000 mL, in portions) was used to dissolve the solid in the filter funnel and the $CH_2Cl_2$ solution was vacuum filtered through the funnel. The $CH_2Cl_2$ solution was transferred to an evaporation flask with the aid of 300 mL of additional $CH_2Cl_2$ and the solution was concentrated to approximately 3500 mL under vacuum (700 mbar, 40–42° C.). Acetic acid (1250 mL) was added with swirling and the $CH_2Cl_2$ was removed under vacuum (700–390 mbar, 42–52° C.). The resulting slurry was cooled to ambient temperature and vacuum filtered on a Buchner funnel with hardened qualitative filter paper. The solid was slurried and rinsed in portions with acetic acid (1000 mL) and then rinsed with 500 mL of ethanol (anhydrous). The product was then dried in a vacuum oven (30" Hg) at 50–62° C. for approximately 58 hours to a constant weight. The solid was transferred to an evaporation flask with $CH_2Cl_2$ (4500 mL) and the mixture was warmed at 35–42° C. for 30 minutes. Ethanol (2500 mL, anhydrous) was added with swirling as the $CH_2Cl_2$ was removed under vacuum (600–340 mbar, 40–50° C.). The resulting slurry was cooled to ambient temperature over 19 minutes.

The product was collected by vacuum filtration on a Buchner funnel with hardened qualitative filter paper, slurried and rinsed in portions with ethanol (1000 mL), and dried in a vacuum oven (30" Hg) at 56–60° C. for 30 hours to a constant weight. The solid was then dried an additional 23 hours to give 148.9 g (90.8% yield) of tin dichloride ethyl etiopurpurin (7) (purity >99% by HPLC).

Example 14

Preparation of Tin dichloride Ethyl Etiopurpurin I (7) (Method C)

The procedure of Example 13 method B was repeated except that acetonitrile replaced ethanol and the volume of acetonitrile used was half that of ethanol. Yield of tin dichloride ethyl etiopurpurin (7)=80%.

Example 15

Preparation of Tin dichloride Ethyl Etiopurpurin (7) (Method D)

The procedure of Example 13 method B was repeated except that dry dimethylformamide replaced ethanol and the volume of dimethylformamide used was half that of ethanol. Yield of tin dichloride ethyl etiopurpurin (7)=70%.

Example 16

Isolation of MET2 (6)

The acetonitrile mother liquors from the ET2 (5) precipitations (Example 8, method A) were rotoevaporated to dryness. The solid was redissolved in dichloroethane (1000 mL) and to this solution was added $SnCl_2$ (20 g; anhydrous) predissolved in DMF (25 mL). Sodium acetate (8 g; anhydrous) was added. The solution was warmed at 55–60° C. for 4 hours after which time the solution was cooled to room temperature and washed with water (2×1000 mL). The organic layer was evaporated to dryness and the residue redissolved in dichloromethane (200 mL). The solution was chromatographed on a short pad of silica (1 Kg), eluting with 5% ethylacetate/dichloromethane. The tin metallated porphyrin impurities remained at the baseline on the column. The major band was collected and recrystallized from dichloromethane/isooctane. Yield of MET2 (6)=27%, purity >98%.

Example 17

Preparation of Octaethylpurpurin (32)

Meso-acrylate octaethylporphyrin (11) (20.4 g, 0.032 mole), toluene (375 mL) and 1,8-diazabicyclo [5.4.0] undec-7-ene (DBU, 2 mL, 0.013 mole) were combined in a 2 L round bottom reaction vessel and purged with argon for 21 minutes, brought to reflux and held for approximately 5 hours under an argon atmosphere. TLC was used to monitor the completion of the reaction. The reaction was cooled to ambient temperature, transferred to an evaporation flask with the aid of additional toluene (20 mL) and the solvent was removed under vacuum (98–30 mbar, 60–70° C.).

Methylene chloride (400 mL) was added to the solid and the mixture was warmed with swirling at 35–41OC for 35 minutes. Acetonitrile (250 mL) was added in portions with swirling as the $CH_2Cl_2$ was removed at reduced pressure (700–408 mbar, 45–55° C.). The slurry was vacuum filtered while still warm on a Buchner funnel with hardened qualitative filter paper and the solid was slurried and rinsed in portions with acetonitrile (175 mL), and then dried until the solid caked. The solid was transferred to an evaporation flask with $CH_2Cl_2$ (400 mL) and the mixture was warmed with swirling at 35–45° C. for 30 minutes. Acetonitrile (250 mL) was added in portions with swirling as the $CH_2Cl_2$ was removed at reduced pressure (695–460 mbar, 45–55° C.). The warm slurry was vacuum filtered on a Buchner funnel with hardened qualitative filter paper and the solid was slurried and rinsed in portions with acetonitrile (150 mL), then dried until the solid caked. The solid was analyzed by TLC to determine the purity and then dried under vacuum (30" Hg) at 52–57° C. for approximately 21 hours to a constant weight to yield 18.3 g (90% yield) of octaethylpurpurin (32).

Example 18

Preparation of Octaethylbenzochlorin (13)-Method A

Meso-acrylate octaethylporphyrin (11) (100 g, 0.16 mole) and dichloromethane (4000 mL) were combined in a 10 L round bottom reaction vessel equipped with a mechanical stirrer and a thermocouple. The solution was purged with nitrogen for 21 minutes. The reaction was cooled to −78° C. under nitrogen using an acetone/$CO_2$ bath. DIBALH (270 mL, 1.5M in toluene) was added dropwise via a dropping funnel to the reaction at a rate as to maintain the temperature between −78° C. and −75° C. After the addition of the DIBALH, the reaction was monitored until all starting material had been consumed [TLC, Acetone/DCM (1%)]. Excess DIBALH was quenched with dropwise addition of isopropanol (100 mL) followed by MeOH (100 mL). $H_3PO_4$ (1800 mL, 85%) was added to the cold solution and the flask warmed to room temperature. The dichloromethane/methanol was distilled and the phosphoric acid solution warmed at 100° C. for 3 hours after which time the reaction was deemed complete by TLC (DCM). The solution was cooled to room temperature and water (2800 mL) was added with vigorous stirring. The solid precipitate was vacuum filtered and rinsed with portions of methanol (3×200 mL), and then dried until the solid caked. The solid was air dried overnight, redissolved in phosphoric acid (85%, 1500 mL) and reprecipitated with water (2500 mL). The crude OEBC was collected by filtration, washed with MeOH (300 mL) and air dried overnight. The solid was dissolved in $CH_2Cl_2$ (2000 mL) into a 5L distillation flask and MeOH (1500 mL) was added. The $CH_2Cl_2$ was removed by distillation with stirring and the solid precipitate was collected by filtration, and washed with MeOH (200 mL). The solid was vacuum dried to constant weight. Yield of octaethylbenzochlorin (13)=69 g (72%).

Example 19

Preparation of Octaethylbenzochlorin (13)-Method B

Nickel (II) octaethylbenzochlorin (1 g, 0.0017mol) was dissolved in dichloromethane (30 mL). Methane sulfonic acid (10 mL) was added and the dichloromethane was removed by rotary evaporation. The methane sulfonic acid solution was warmed to 80° C. under nitrogen and the reaction monitored hourly until complete by TLC (after neutralization of a small aliquot, 30% hexane/DCM). Once complete, the solution was diluted with ice cold water (15 mL) and the solid precipitate collected by filtration and washed with MeOH (30 mL). The solid was redissolved in dichloromethane (50 mL) and MeOH (50 mL) was added. The dichloromethane was removed by rotoevaporation and the solid collected by filtration and washed with MeOH (20 mL). Yield of octaethylbenzochlorin (13)=0.7 g (73%). The solid was sufficiently pure to be used further, if desired. Additional OEBC may be isolated from the methanol mother liquors by chromatography if required.

Example 20

Tin Dichloride Pheophorbide Methyl Ester (21)

Pyropheophorbide methyl ester (20) (1.0 g) was dissolved in glacial acetic acid (100 ml) and sodium acetate (0.74 g, anhydrous) was added. $SnCl_2$ (2.4 g, anhydrous) was predissolved in dimethylformamide (5 mL) and added to the solution. A wide bore glass bubbling tube was added to the reaction vessel such that air was efficiently purged into the bottom of the acetic acid solution. A moderate stream of air was bubbled through the solution over the entire reaction. The solution was heated to 105–110° C. until the reaction was complete by UVNis and by TLC (1% acetone/dichloromethane). The reaction was cooled and the acetic acid was removed by rotoevaporation. The residue was dissolved in dichloromethane (100 L) and washed several times with 1N HCl solution (4×100 L). The organic layer was collected and dried over sodium sulfate. The organic layer was filtered and evaporated to dryness. The residue was dissolved in dichloromethane (50 L) and ethanol (50 L) was added. The dichloromethane was removed by rotary evaporation and the precipitated product (21) collected by filtration and dried under high vacuum. Yield=1.21 g (90%); Purity >98% by HPLC.

Example 21

Tin Dichloride Meso-acrylate Etioporphyrin I (25)

$SnCl_2$ (6.54 g, anhydrous) was dissolved in dimethylformamide (8 mL). Dichloroethane (200 mL) was added to the tin solution and sodium acetate (1.54 g, anhydrous) was added. The solution was stirred at 30° C. for 30 minutes with compressed air bubbling through the solution moderately via a wide bore glass tube. Meso-acrylate etioporphyrin I (4.0 g) dissolved in dichloroethane (80 mL) was added slowly to the solution and the solution warmed at 55–60° C. for 5 hours until complete by TLC. (2% acetone/dichloromethane). The solution was cooled and filtered to remove excess salts. The salts were washed with a small amount of dichloromethane (20 mL). The combined organic solution was washed three times with dilute HCl (1N). The organic layer was dried over sodium sulfate and filtered. The sodium sulfate was washed with a small amount of dichloromethane (20 mL). The solvent was removed by rotary evaporation and the crude residue dissolved in dichloromethane (50 mL) and acetic acid (50 mL) was added. The dichloromethane was removed by rotary evaporation and the solid precipitate was collected by filtration and dried under high vacuum. Yield of tin dichloride meso-acrylate etioporphyrin I (25)=3.7 g (70%). An HPLC of the material showed it to be >98% pure with no reduced porphyrin (26).

Example 22

Tin Dichloride Protoporphyrin IX, Dimethyl Ester (28)

Protoporphyrin IX dimethyl ester (27) (5.0 g) was dissolved in pyridine (200 mL). $SnCl_2$ (8.0 g, anhydrous) was added and the solution was aerated with compressed air moderately bubbling through the solution via a wide bore glass tube. The solution was heated to 100° C. for 3 hours after which the reaction was cooled to room temperature. The pyridine was removed by rotary evaporation and the residue dissolved in dichloromethane (500 mL) and washed three times with dilute HCl (1N, 100 mL). The organic layer was dried over sodium sulfate, filtered and evaporated to approximately 100 mL. Acetic acid (100 mL) was added and the dichloromethane was removed by rotary evaporation. The precipitated solid was collected by filtration and dried under high vacuum. Yield of tin dichloride protoporphyrin IX, dimethyl ester (28)=4.7 g (71%). Analysis of the product showed it to be >99% pure.

It will be apparent to those skilled in the art that various modifications and variations can be made in the compounds and methods of the present invention without departing from the spirit or scope of the invention. Thus, it is intended that the present description cover the modifications and variations of this invention provided that they come within the scope of the appended claims and their equivalents.

What we claim is:

1. A process for isolating a mono-formylated tetrapyrrolic compound comprising:
   a) contacting a reaction product containing mono- and di-formylated tetrapyrrolic compounds with a solvent to form a solution thereof;
   b) adding an alkylcarboxylic acid precipitating solvent to the solution;
   c) distilling all or a sufficient portion of the first solvent from the solution to precipitate from the solution formylated tetrapyrrolic compounds having a smaller proportion of di-formylated tetrapyrrolic compounds than was present in the reaction product; and d) isolating formylated tetrapyrrolic compounds from the resulting distillate having a smaller proportion of di-formylated tetrapyrrolic compounds than was present in the reaction product.

2. The process of claim 1, wherein steps a), b), c), and d) are repeated.

3. The process of claim 1, wherein the solvent is selected from dichloroethane, dichloromethane, ethyl acetate, tetrahydrofuran, acetonitrile, acetone, benzene, toluene and ether.

4. The process of claim 3, wherein the precipitating solvent is selected from acetic acid, propionic acid, butyric acid, pentanoic acid, hexanoic acid, heptanoic acid, and octanoic acid.

5. The process of claim 4, wherein the solvent is methylene chloride and the precipitating solvent is acetic acid.

6. The process of claim 1, wherein the formyl tetrapyrrolic compound is a meso-formylated tetrapyrrolic compound.

7. The process of claim 1, wherein the formyl tetrapyrrolic compound is a β-formylated tetrapyrrolic compound.

8. The process of claim 1, wherein the formyl tetrapyrrolic compound is Nickel (II) meso-formyl etioporphyrin I.

9. The process of claim 1, wherein the formyl tetrapyrrolic compound is Nickel (II) meso-formyl octaethylporphyrin.

10. The process of claim 1, wherein the formyl tetrapyrrolic compound is a metallo-derivative with Copper (II) or Nickel (II) bound to the central inner nitrogens.

11. The process of claim 1, wherein the formyl tetrapyrrolic compound is a meso-formyl porphyrin selected from Copper (II) etioporphyrin I, Nickel (II) etioporphyrin I, Copper (II) etioporphyrin II, Nickel (II) etioporphyrin II, Copper (II) octaethylporphyrin, Nickel (II) octaethylporphyrin I, Copper (II) coproporphyrin I tetra-alkyl ester, Nickel (II) coproporphyrin I tetra-alkyl ester, Copper (II) coproporphyrn II tetra-alkyl ester, Nickel (II) coproporphyrin II tetra-alkyl ester, Copper (II) mesoporphyrin di-alkyl ester, Nickel (II) mesoporphyrin di-alkyl ester, Nickel β-formyl tetraphenyl porphyrin, Nickel β-formyl tetrakis((4'-methyl)phenyl))porphyrin, and Nickel β-formyl tetrakis((4'-carbomethoxy)phenyl) porphyrin.

12. The process of claim 1, wherein the formyl tetrapyrrolic compound is selected from a metallo-meso-formyl chlorin, a metallo-meso-formyl bacteriochlorin, a metallo-meso-formyl iso-bacteriochlorin, a metallo-meso-formyl corrole, a metallo-meso-formyl porphyracene, and a metallo-meso-formyl azaporphyrin.

13. The process of claim 6, wherein the formyl tetrapyrrolic compound is selected from a meso-formyl chlorine a meso-formyl bacteriochlorin, a meso-formyl iso-bacteriochlorin, a meso-formyl corrole, a meso-formyl porphyracene, and a meso-formyl azaporphyrin.

14. A process for formylating a metallo-tetrapyrrolic compound comprising:
   a) dissolving or partially dissolving a reaction product containing a metallo-tetrapyrrolic compound in a solvent that includes dichloromethane;
   b) adding a Vilsmeier reagent to the reaction product mixture;
   c) heating the reaction product mixture to a temperature and at a pressure sufficient to form the iminium salt intermediate of the metallo-tetrapyrrolic compound;
   d) hydrolyzing the resulting tetrapyrrolic iminium salt at a temperature and pressure sufficient to produce the desired formyl metallo-tetrapyrrolic compound.

15. The process of claim 14, wherein the metallo-tetrapyrrolic reaction product mixture is heated past the boiling point of the solvent or solvents.

16. The process of claim 14, wherein the solvent is dichloromethane.

17. The process of claim 14, wherein the temperature of the reaction product mixture is maintained at 35–65° C. during the Vilsmeier reaction.

18. The process of claim 17, wherein the temperature of the reaction product mixture is maintained at 50–60° C. during the Vilsmeier reaction.

19. The process of claim 14, wherein the metallo-tetrapyrrolic compound is selected from Nickel (II) etioporphyrin I, Nickel (II) octaethylporphyrin, and Nickel (II) coproporphyrin I tetraalkyl ester.

20. A process for formylating a metallo-tetrapyrrolic compound comprising:
   a) dissolving or partially dissolving a metallo-tetrapyrrolic reaction product in dichloromethane;
   b) adding a Vilsmeier reagent to the metallo-tetrapyrrolic reaction product mixture;
   c) refluxing the solution at a temperature and pressure sufficient to form the iminium salt intermediate of the metallo-tetrapyrrolic compound;
   d) hydrolyzing the resulting tetrapyrrole iminium salt at a temperature and pressure sufficient to produce the desired formyl tetrapyrrolic compound.

21. The process of claim 20, wherein the metallated tetrapyrrolic compound is selected from Nickel (II) etioporphyrin I, Nickel (II) octaethylporphyrin, and Nickel (II) coproporphyrin I tetraalkyl ester.

22. The process of claim 20, wherein the metallated tetrapyrrolic compound has a symmetrical peripheral substitution pattern.

23. A process for producing a mono- or di-acrylate tetrapyrrolic compound comprising:
   a) contacting a mono- or di-formyl tetrapyrrolic compound, a Wittig reagent, and dimethylformamide to form a slurry;
   b) melting the slurry under an inert atmosphere at a temperature sufficient to produce the corresponding mono or di-acrylate tetrapyrrolic product.

24. The process of claim 23, wherein the weight of dimethylformamide ranges from about 90% to about 110% of the weight of the starting mono or di-formyl tetrapyrrole.

25. The process of claim 23, wherein the dimethylformamide functions to keep any unreacted Wittig or mono- or diformyl tetrapyrrolic compound in the reaction melt.

26. A process for isolating a mono or di-acrylate tetrapyrrolic compound comprising:
   a) contacting a reaction product containing a mono or di-acrylate tetrapyrrolic compound with a solvent to form a solution thereof;
   b) adding a precipitating solvent to the solution;
   c) distilling a portion of the solvent from the solution;
   d) isolating the mono or di-acrylate tetrapyrrolic compound from the resulting solution.

27. The process of claim 26, wherein the steps a), b), c), d) are repeated.

28. The process of claim 26, wherein both the solvent and the precipitating solvent are halogenated solvents.

29. The process of claim 26, wherein the solvent is a non-halogenated solvent and the precipitating solvent is a halogenated solvent.

30. The process of claim 26, wherein both the solvent and the precipitating solvent are non-halogenated solvents.

31. The process of claim 26, wherein the solvent is a halogenated solvent and the precipitating solvent is a non-halogenated solvent.

32. The process of claim 26, wherein the solvent is selected from dichloroethane, dichloromethane, ethyl acetate, tetrahydrofuran, acetonitrile, acetone, benzene, toluene and ether.

33. The process of claim 26, wherein the precipitating solvent is selected from acetic acid, propionic acid, methanol, ethanol, 1-propanol, 2-propanol, 1-butanol, hexanes, acetonitrile, ethyl acetate and iso-octane.

34. The process of claim 26, wherein the solvent is methylene chloride and the precipitating solvent is ethanol or methanol.

35. The process of claim 26, wherein the mono- or di-acrylate tetrapyrrolic compound is a mono or di-meso-acrylate tetrapyrrolic compound.

36. The process of claim 26, wherein the mono or di-acrylate tetrapyrrolic compound is a β-substituted mono or di-acrylate tetrapyrrolic compound.

37. The process of claim 26, wherein the mono or di-acrylate tetrapyrrolic compound is both β- and meso-acrylate substituted.

38. The process of claim 26, wherein the mono-acrylate tetrapyrrolic compound is selected from Nickel (II) meso-acrylate etioporphyrin I, Nickel (II) meso-acrylate octaethylporphyrin, Nickel (II) meso-acrylate coproporphyrin I tetra ester, Copper (II) meso-acrylate etioporphyrin I, Copper (II) meso-acrylate octaethylporphyrin, and Copper (II) meso-acrylate coproporphyrin I tetra ester.

39. The process of claim 26, wherein the di-acrylate tetrapyrrolic compound is selected from Nickel (II) 5,15-diacrylate etioporphyrin I, Nickel (II) 5,10-diacrylate etioporphyrin I, Nickel (II) 5,15-diacrylate octaethylporphyrin, Nickel (II) 5,10-diacrylate octaethylporphyrin, Nickel (II) 5,15diacrylate coproporphyrin I tetra ester, Nickel (II) 5,10-coproporphyrin I tetra ester, Copper (II) 5,15-diacrylate octaethylporphyrin, Copper (II) 5,10-diacrylate octaethylporphyrin, Copper (II) 5,15-diacrylate coproporphyrin I tetra ester, and Copper (II) 5,10-diacrylate coproporphyrin I tetra ester.

40. The process of claim 26, wherein the mono or di-acrylate tetrapyrrolic compound is a metallo-derivative with Copper (II) or Nickel (II) bound to the central inner nitrogens.

41. The process of claim 26, wherein the precipitating solvent decreases the amount of impurities in the resulting product.

42. The process of claim 26, wherein the mono-acrylate tetrapyrrolic compound is a metallo-mono-meso-acrylate porphyrin selected from Copper (II) meso-formyl copropor-phyrin I tetra ester, Nickel (II) meso-formyl coproporphyrin I tetra ester, Copper (II) meso-formyl coproporphyrin II tetra ester, Nickel (II) meso-formyl coproporphyrin II tetra ester, Copper (II) meso-formyl mesoporphyrin di-ester, and Nickel (II) meso-formyl mesoporphyrin di-ester.

43. The process of claim 26, wherein the mono or di-acrylate tetrapyrrolic compound is selected from a metallo-mono- or di-acrylate chlorin, a metallo-mono- or di-acrylate bacteriochlorin, a metallo-mono- or di-acrylate iso-bacteriochlorin, a metallo-mono- or di-acrylate corrole, a metallo-mono- or di-acrylate porphyracene, and a metallo-mono- or di-acrylate azoporphyrin.

44. A process for demetallating a metallo-tetrapyrrolic compound comprising:
a) dissolving the metallo-tetrapyrrolic compound in a solvent or mixture of solvents that is not water soluble;
b) adding an acid capable of removing the central co-ordinated metal of the metallo-tetrapyrrolic compound to the solvent or mixture of solvents containing the metallo-tetrapyrrolic compound with stirring or agitation; and
c) waiting a period of time sufficient to effect the demetallation.

45. The process of claim 44, wherein said demetallation is effected when the solvent or mixture of solvents becomes essentially colorless.

46. The process of claim 44 wherein the solvent or mixture of solvents is selected from dichloromethane, chloroform, 1,2-dichloroethane, 1,1-dichloroethane, toluene, xylene, benzene, hexane, and ether.

47. The process of claim 44, wherein the acid is selected from sulfuric acid, hydrochloric acid, and phosphoric acid.

48. The process of claim 44, wherein the weight of acid added ranges from about 90% to about 110% of the initial dry weight of the metallo-tetrapyrrolic compound.

49. The process of claim 44, wherein the metallo-tetrapyrrolic compound is selected from Nickel (II) meso-acrylate etioporphyrin I, Copper (II) meso-acrylate etioporphyrin I, Nickel (II) meso-acrylate octaethylporphyrin, Copper (II) meso-acrylate octaethylporphyrin, Nickel (II) meso-acrylate coproporphyrin I or II tetra-ester, and Copper (II) meso-acrylate coproporphyrin I or II tetra ester.

50. The process of claim 49, wherein the metallo-tetrapyrrolic compound is a metallated di-acrylate porphyrin.

51. A process for demetallating a metallo-tetrapyrrolic compound comprising:
a) adding an acid capable of removing the central co-ordinated metal of a metallo-tetrapyrrolic compound to a reactor vessel with stirring or agitation;
b) dissolving a metallo-tetrapyrrolic compound in a solvent or mixture of solvents that is not water soluble;
c) adding the solution of metallo-tetrapyrrolic compound to the reactor vessel containing the acid with stirring or agitation; and
d) waiting a period of time sufficient to effect said demetallation.

52. The process of claim 51, wherein said demetallation is effected when the solvent or mixture of solvents becomes essentially colorless.

53. The process of claim 51, wherein the solvent or mixture of solvents is selected from dichloromethane, chloroform, 1,2-dichloroethane, 1,1-dichloroethane, toluene, xylene, benzene, hexane, and ether.

54. The process of claim 51, wherein the acid is selected from sulfuric acid, hydrochloric acid, and phosphoric acid.

55. The process of claim 51, wherein the weight of acid added ranges from about 90% to about 110% of the initial dry weight of the metallo-tetrapyrrolic compound.

56. The process of claim 51, wherein the metallo-tetrapyrrolic compound is selected from Nickel (II) meso-acrylate etioporphyrin I, Copper (II) meso-acrylate etioporphyrin I, Nickel (II) meso-acrylate octaethylporphyrin, Copper (II) meso-acrylate octaethylporphyrin, Nickel (II) meso-acrylate coproporphyrin I or II tetra-ester, and Copper (II) meso-acrylate coproporphyrin I or II tetra ester.

57. The process of claim 51, wherein the metallo-tetrapyrrolic compound is a metallated di-acrylate porphyrin.

58. A process for demetallating a metallo-tetrapyrrolic compound comprising:
a) forming a solution of a metallo-tetrapyrrole in a solvent or mixture of solvents that is not water soluble;
b) simultaneously adding said solution and an acid that is capable of removing the central co-ordinated metal of a metallo-tetrapyrrolic compound to a reactor vessel with stirring or agitation; and c) waiting a period of time sufficient to effect said demetallation.

59. The process of claim 58, wherein said demetallation is effected when the solvent or mixture of solvents becomes essentially colorless.

60. The process of claim 58, wherein the acid is selected from sulfuric acid, hydrochloric acid, and phosphoric acid.

61. The process of claim 58, wherein the weight of acid added ranges from about 90% to about 110% of the initial dry weight of the metallo-tetrapyrrolic compound.

62. The process of claim 58, wherein the metallo-tetrapyrrolic compound is selected from Nickel (II) meso-acrylate etioporphyrin I, Copper (II) meso-acrylate etioporphyrin I, Nickel (II) meso-acrylate octaethylporphyrin, Copper (II) meso-acrylate octaethylporphyrin, Nickel (II) meso-acrylate coproporphyrin I or II tetra-ester, and Copper (II) meso-acrylate coproporphyrin I or II tetra ester.

63. The process of claim 62, wherein the metallo-tetrapyrrolic compound is a metallated di-acrylate porphyrin.

64. A process for isolating a mono or di-acrylate tetrapyrrolic compound from a demetallation reaction mixture comprising:

a) adding water to a reaction mixture containing a solvent or mixture of solvents that is not water soluble, a demetallated tetrapyrrolic compound, and an acid;

b) neutralizing or partially neutralizing the aqueous phase of the mixture;

c) separating the organic phase of the mixture from the aqueous phase;

d) adding a precipitating solvent or mixture of precipitating solvents to the organic phase;

e) distilling the solvent or mixture of solvents at least partially from the reaction mixture to induce precipitation or crystallization; and f) separating the solid from the remaining solution and isolating the desired mono or di-acrylate tetrapyrrolic compound.

65. The process of claim 64, wherein steps a), b), c), d) are repeated.

66. The process of claim 64, wherein both the solvent or mixture of solvents and the precipitating solvent or mixture of solvents includes a halogenated solvent.

67. The process of claim 64, wherein the solvent or mixture of solvents includes a non-halogenated solvent and the precipitating solvent or mixture of solvents includes a halogenated solvent.

68. The process of claim 64, wherein both the solvent or mixture of solvents and the precipitating solvent or mixture of solvents includes a non-halogenated solvent.

69. The process of claim 64, wherein the solvent or mixture of solvents includes a halogenated solvent and the precipitating solvent or mixture of solvents includes a non-halogenated solvent.

70. The process of claim 64, wherein the solvent is methylene chloride and the precipitating solvent is ethanol or methanol.

71. The process of claim 64, wherein the mono- or di-acrylate tetrapyrrole is a mono or di-meso-acrylate tetrapyrrolic compound.

72. The process of claim 64, wherein the mono or di-acrylate tetrapyrrolic compound is a β-substituted mono or di-acrylate tetrapyrrolic compound.

73. The process of claim 64, wherein the mono or di-acrylate tetrapyrrolic compound is β- and meso-acrylate substituted.

74. A process for cyclizing a mono-meso-acrylate tetrapyrrolic compound to the corresponding purpurin comprising heating a solution of a mono-meso-acrylate tetrapyrrolic molecule in a solvent or mixture of solvents having a boiling point greater than about 80° C. in the presence of a non-nucleophilic base with a pKa greater than about 10.8 under conditions sufficient to form the cyclized purpurin.

75. The process of claim 74, wherein said non-nucleophilic base is selected from 1,5-diazabicyclo[4.3.2]non-5-ene, 1,8-diazabicyclo[5.4.0]undec-7-ene, tetramethylguanidine, piperidine, and pyrrolidine.

76. The process of claim 74, wherein the solvent is toluene.

77. A process for isolating a purpurin from an acetic acid or base catalyzed cyclization reaction of a tetrapyrrolic compound comprising:

a) removing all or substantially all of the liquid from the cyclization reaction product;

b) forming a solution of the remaining reaction product in a solvent or mixture of solvents;

c) adding a precipitating solvent or mixture of solvents to the solution;

d) removing the solvent or mixture of solvents at least partially from the reaction mixture to induce precipitation or crystallization of the desired purpurin;

e) separating the solid from the remaining solution and isolating the desired purpurin compound.

78. The process of claim 77, wherein steps b), c), d), e) are repeated.

79. The process of claim 77, wherein the solvent or mixture of solvents contains a halogenated solvent and the precipitating solvent or mixture of solvents contains a non-halogenated solvent.

80. The process of claim 77, wherein the both the solvent or mixture of solvents and the precipitating solvent or mixture of solvents contain a halogenated solvent.

81. The process of claim 77, wherein both the solvent or mixture of solvents and the precipitating solvent or mixture of solvents contain a non-halogenated solvent.

82. The process of claim 77, wherein the solvent or mixture of solvents contains a non-halogenated solvent and the precipitating solvent or mixture of solvents contains a halogenated solvent.

83. The process of claim 77, wherein the solvent or mixture of solvents is selected from dichloromethane, ether, 1,2-dichloroethane, chloroform, toluene, acetone, tetrahydrofuran, ethyl acetate, and benzene.

84. The process of claim 77, wherein the precipitating solvent is selected from methanol, ethanol, 1-propanol, 2-propanol, 1-butanol, acetone, acetonitrile, hexane, heptane, octane, cyclohexane, and isopropyl ether.

85. The process of claim 77, wherein the solvent is dichloromethane and the precipitating solvent is acetonitrile or acetone.

86. The process of claim 77, wherein the isolated purpurin is ethyl etiopurpurin I, the solvent is dichloromethane, and the precipitating solvent is acetonitrile.

87. The process of claim 77, wherein the isolated purpurin is ethyl etiopurpurin I, the solvent is dichloromethane and the precipitating solvent is acetone.

88. A process for isolating methyl etiopurpurin from a base catalyzed or acetic acid catalyzed cyclization reaction of meso-acrylate etioporphyrin I comprising:

a) removing all or substantially all of the liquid from the cyclization reaction;

b) forming a solution of the remaining reaction product in a first solvent or mixture of solvents;

c) adding sodium acetate and a solution of stannous chloride or stannous acetate predissolved in dimethylformamide to the solution;

d) warming the solution to about 30–80° C. until no more meso-acrylate etioporphyrin I or metal free porphyrinic impurities are visible by TLC;

e) distilling the solution at atmospheric or reduced pressure to remove all or substantially all of the liquid;

f) redissolving the crude solid in a second solvent or mixtures of solvents;

g) passing the solution over a silica gel or alumina column, while eluting with a third solvent or mixture of solvents and collecting the purpurin fraction thereby removing the highly polar tin porphyrin impurities from the crude reaction mixture;

h) distilling the solution to remove all or substantially all of the liquid from the purpurin fraction at atmospheric or reduced pressure;

i) redissolving the remaining solid in a fourth solvent;

j) adding a precipitating solvent or mixture of solvents and distilling all or substantially all of the fourth solvent from the solution to induce precipitation of the methyl etiopurpurin; and k) isolating the methyl etiopurpurin by filtration.

89. The process of claim 88, wherein the first solvent or mixture of solvents is selected from 1,2-dichloromethane, acetic acid, and propionic acid; the second solvent is selected from dichloromethane, a dichloromethane/ethylacetate mixture, a dichloromethane/methanol mixture, a dichloromethane/acetone mixture, and a dichloromethane/ethanol mixture; the third solvent is selected from a dichloromethane/ethylacetate mixture, a dichloromethane/methanol mixture, a dichloromethane/acetone mixture, and a dichloromethane/ethanol mixture; the fourth solvent is selected from dichloromethane, tetrahydrofuran, and ether; and the precipitating solvent is selected from methanol, ethanol, 1-butanol, t-butanol, 1-propanol, 2-propanol, isooctane, isopropyl ether, and hexane.

90. The process of claim 88 wherein steps i), j), and k), are repeated more than once.

91. A process for reducing the ester of an ester-containing tetrapyrrolic compound comprising:

a) dissolving the ester-containing tetrapyrrolic compound in a first cholorinated solvent or mixture of solvents;

b) adding diisobutylaluminium hydride in toluene to the solution to reduce the ester to the corresponding alcohol; and c) quenching the reaction with a second solvent or mixture of solvents.

92. The process of claim 91, wherein the tetrapyrrolic molecule is selected from esters of protoporphyrin IX, esters of mesoporphyrin IX, esters of meso-acrylate etioporphyrin I, esters of meso-acrylate octaethylporphyrin, and esters of meso-acrylate coproporphyrin I or II.

93. The process of claim 91, wherein the first solvent is selected from dichloromethane and 1,2-dichloroethane.

94. The process of claim 91, wherein the second solvent is selected from isopropanol and methanol.

95. The process of claim 91, wherein the reaction is carried out at a temperature ranging from about −80° C. to about −35° C.

96. A process for converting the ester of a meso-acrylate tetrapyrrolic compound to a benzochlorin comprising:

a) dissolving the meso-acrylate tetrapyrrolic compound in a first solvent or mixture of solvents;

b) adding diisobutylaluminium hydride in toluene to the tetrapyrrolic molecule in the first solvent or mixture of solvents;

c) quenching the reaction with a second solvent or mixture of solvents;

d) adding an acid or mixture of acids to the solution and distilling off the organic solvents from the reaction while the temperature of the reaction is increased to about 60–130° C.;

e) holding the reaction at 60–130° C. until no more starting material remains;

f) adding an amount of water to the reaction sufficient to selectively precipitate the benzochlorin, while leaving impurities in the acidic aqueous solution;

g) isolating the benzochlorin by filtration;

h) dissolving the crude benzochlorin in a third solvent or mixture of solvents;

i) adding a precipitating solvent or mixture of solvents and distilling at least part of the third solvent from the reaction to induce precipitation of the benzochlorin; and j) isolating the benzochlorin by filtration.

97. The process of claim 96, wherein the meso-acrylate tetrapyrrolic molecule is selected from an ester of a meso-acrylate octaalkylporphyrin, an ester of a meso-acrylate octaethylporphyrin, an ester of meso-acrylate etioporphyrin I or II, and an ester of meso-acrylate coproporphyrin I or II.

98. The process of claim 96, wherein the first solvent or mixture of solvents is selected from dichloromethane, tetrahydrofuran, toluene, and dichloroethane.

99. The process of claim 96, wherein the second solvent or mixture of solvents contains an alcohol, an ester, an acid or water.

100. The process of claim 96, wherein the acid or mixture of acids is selected from phosphoric acid, methane sulfonic acid, and hydrochloric acid.

101. The process of claim 96, wherein the fourth solvent or mixture of solvents is selected from dichloromethane, tetrahydrofuran, toluene, dichloroethane, acetone, benzene, N,N-dimethylformamide, acetonitrile, and xylene.

102. The process of claim 96, wherein the precipitating solvent or mixture of solvents in step i) is selected from water, alcohol, hexane, isopropyl ether, iso-octane, and acetonitrile.

103. The process of claim 96, wherein the precipitating solvent is also used to wash the benzochlorin in each of steps g) and j).

104. A method for cyclizing a meso-((2-hydroxymethyl)vinyl)porphyrin or an alcohol protected derivative thereof to a benzochlorin comprising contacting the meso-((2-hydroxymethyl)vinyl)porphyrin or an alcohol protected derivative thereof with an acid catalyst selected from phosphoric acid, methane sulfonic acid, and hydrochloric acid under conditions sufficient to effect the cyclization reaction.

105. A method for cyclizing a meso-((2-hydroxymethyl)vinyl)tetrapyrrolic compound or an alcohol protected derivative thereof to form a tetrapyrrolic compound possessing an annelated six membered ring comprising contacting the meso-((2-hydroxymethyl)vinyl)tetrapyrrolic compound or an alcohol protected derivative thereof with an acid catalyst selected from phosphoric acid, methane sulfonic acid, and hydrochloric acid under conditions sufficient to effect the cyclization reaction.

106. A method of demetallating a metallo-benzochlorin compound comprising contacting the metallo-benzochlorin compound with methane sulfonic acid for a time and at a temperature sufficient to achieve demetallation.

107. A method of demetallating a metallo-isobacteriobenzochlorin or a metallo-bacteriobenzochlorin compound comprising contacting the metallo-isobacteriobenzochlorin or metallo-bacteriobenzochlorin compound with methane sulfonic acid for a time and at a temperature sufficient to achieve demetallation.

108. A method for producing a tin (IV) tetrapyrrolic complex from the corresponding non-metallated compound comprising: (a) contacting the non-metallated tetrapyrrolic compound with a solvent; and (b) bubbling an oxygen containing gas into the solvent before or after the non-metallated tetrapyrrolic compound is contacted by the solvent.

109. A method for producing a tin (IV) tetrapyrrolic complex comprising:
   a) dissolving or suspending a metal free tetrapyrrolic macrocycle in a solvent or mixture of solvents;
   b) adding a tin salt and a proton scavenger to the solvent or mixture of solvents before or after step (a);
   c) introducing an oxygen containing gas into the solvent or mixture of solvents before or after step (a); and
   d) heating the solution or suspension in the presence of the tin salt and the proton scavenger under conditions sufficient to form the tin (IV) tetrapyrrolic complex.

110. The method of claim 109, wherein the solvent or mixture of solvents is selected from acetic acid, propionic acid, pyridine, dimethylformamide, 1,2-dichloroethane, chloroform, 1,1-dichloroethane, and a halogenated solvent.

111. The method of claim 109, wherein the tin salt is selected from $SnCl_2$, $Sn(OAc)_2$, and $Sn(acac)_2$.

112. The method of claim 109, wherein the proton scavenger is sodium acetate.

113. A method for producing a tin (IV) tetrapyrrolic complex comprising:
   a) dissolving or suspending a metal free tetrapyrrolic macrocycle in a first solvent or mixture of solvents;
   b) adding a tin salt pre-dissolved in a second solvent and a proton scavenger to the first solvent or mixture of solvents before or after step (a);
   c) introducing an oxygen containing gas into the first solvent or mixture of solvents before or after step (a); and
   d) heating the solution or suspension in the presence of the tin salt and the proton scavenger under conditions sufficient to form the tin (IV) tetrapyrrolic complex.

114. The method of claim 113, wherein the first and second solvents are selected from acetic acid, propionic acid, pyridine, and dimethylformamide.

115. The method of claim 113, wherein the first and second solvents are different.

116. The method of claim 113, wherein the first and second solvents are the same.

117. The method of claim 113, wherein the proton scavenger is sodium acetate.

118. A method for producing a tin (IV) tetrapyrrolic complex comprising:
   a) adding a solid or pre-dissolved tin salt to a solvent;
   b) heating the combination of solvent and tin salt to form a heated solution;
   c) introducing an oxygen containing gas into the solvent before or after step (a); and
   d) adding a metal free tetrapyrrolic macrocycle to the solution under conditions sufficient to form the tin (IV) tetrapyrrolic complex.

119. The method of claim 118, wherein the solvent and predissolving solvent are selected from acetic acid, propionic acid, pyridine, and dimethylformamide.

120. The method of claim 118, wherein the tin salt is selected from $SnCl_2$, $Sn(OAc)_2$, and $Sn(acac)_4$.

121. The method of claim 118, wherein a proton scavenger is added to the solvent prior to or during step (d).

122. The method of claim 121, wherein the proton scavenger is sodium acetate.

123. A method for producing a tin (IV) tetrapyrrolic complex comprising:
   a) dissolving or suspending a cadmium tetrapyrrolic macrocycle in a solvent or mixture of solvents;
   b) adding a tin salt and a proton scavenger to the solvent;
   c) introducing an oxygen containing gas into the solvent before or after step (a); and
   d) heating the solution or suspension under conditions sufficient to form the tin (IV) tetrapyrrolic complex.

124. The method of claim 123, wherein the solvent or mixture of solvents is selected from acetic acid, propionic acid, pyridine, and dimethylformamide.

125. The method of claim 123, wherein the tin salt is selected from $SnCl_2$, $Sn(OAc)_2$, and $Sn(acac)_4$.

126. A method for producing a tin (IV) tetrapyrrolic complex comprising:
   a) dissolving or suspending a cadmium tetrapyrrolic macrocycle in a solvent or mixture of solvents;
   b) adding a solid or pre-dissolved tin salt to a solvent;
   c) introducing an oxygen containing gas into the solvent before or after step (a); and
   d) heating the solution or suspension under conditions sufficient to form the tin (IV) tetrapyrrolic complex.

127. The method of claim 126, wherein a proton scavenger is added to the solvent prior to or during step (d).

128. The method of claim 126, wherein the solvent or mixture of solvents and the pre-dissolving solvent are selected from acetic acid, propionic acid, pyridine, and dimethylformamide.

129. The method of claim 128, wherein the solvent and pre-dissolving solvent are different.

130. The method of claim 128, wherein the solvent and pre-dissolving solvent are the same.

131. The method of claim 126, wherein the tin salt is selected from $SnCl_2$, $Sn(OAc)_2$, and $Sn(acac)_4$.

132. A method for producing a tin (IV) tetrapyrrolic complex comprising:
   a) adding a solid or predissolved tin salt to a solvent;
   b) heating the tin salt and solvent to form a heated solution;
   c) introducing an oxygen containing gas into the solvent before or after step (a); and
   d) adding a cadmium tetrapyrrolic macrocycle to the tin containing solution containing under conditions sufficient to form the tin (IV) tetrapyrrolic complex.

133. The method of claim 132, wherein a proton scavenger is added to the solvent prior to or during step (d).

134. The method of claim 132, wherein the solvent and predissolving solvent are selected from acetic acid, propionic acid, pyridine, and dimethylformamide.

135. The method of claim 132, wherein the tin salt is selected from $SnCl_2$, $Sn(OAc)_2$, and $Sn(acac)_4$.

136. The method of claim 109, wherein the metal free tetrapyrroie is selected from ethyl etiopurpurin I, protoporphyrin IX, a protoporphyrin IX ester, a protoporphyrin IX amide, octaethyl benzochlorin, and methyl pyropheophorbide.

137. The method of claim 113, wherein the metal free tetrapyrrole is selected from ethyl etiopurpurin I, protoporphyrin IX, a protoporphyrin IX ester, a protoporphyrin IX amide, octaethyl benzochlorin, and methyl pyrropheophorbide.

138. The method of claim 118, wherein the metal free tetrapyrrole is selected from ethyl etiopurpurin I, protoporphyrin IX, a protoporphyrin IX ester, a protoporphyrin IX amide, octaethyl benzochlorin, and methyl pyrropheophorbide.

139. The method of claim 109, wherein the metal free tetrapyrrole is selected from a porphyrin, a corrole, a chlorin, a bacteriochlorin, and an iso-bacteriochlorin.

140. The method of claim 113, wherein the metal free tetrapyrrole is selected from a porphyrin, a corrole, a chlorin, a bacteriochlorin, and an iso-bacteriochlorin.

141. The method of claim 118, wherein the metal free tetrapyrrole is selected from a porphyrin, a corrole, a chlorin, a bacteriochlorin, and an iso-bacteriochlorin.

142. The method of claim 109, wherein the metal free tetrapyrrole is selected from a pheophorbide derivative, a purpurin derivative, a benzochlorin derivative, a benzoporphyrin derivative, a chlorin e6 derivative, a chlorin e4 derivative, a rhodin g7 derivative, a bacteriochlorin e6 derivative, and a bacteriopheophorbide derivative.

143. The method of claim 113, wherein the metal free tetrapyrrole is selected from a pheophorbide derivative, a purpurin derivative, a benzochlorin derivative, a benzoporphyrin derivative, a chlorin e6 derivative, a chlorin e4 derivative, a rhodin g7 derivative, a bacteriochlorin e6 derivative, and a bacteriopheophorbide derivative.

144. The method of claim 118, wherein the metal free tetrapyrrole is selected from a pheophorbide derivative, a purpurin derivative, a benzochlorin derivative, a benzoporphyrin derivative, a chlorin e6 derivative, a chlorin e4 derivative, a rhodin g7 derivative, a bacteriochlorin e6 derivative, and a bacteriopheophorbide derivative.

145. A method of recrystallizing or reprecipitating a tin tetrapyrrolic compound comprising:

a) dissolving the tin tetrapyrrolic compound in a solvent or mixture of solvents;

b) adding a precipitating solvent to the solution; and c) removing the solvent or mixture of solvents by distillation or evaporation under conditions sufficient to effect crystallization or precipitation of the tin tetrapyrrolic compound from the solution.

146. The method of claim 145, wherein the tin tetrapyrrolic compound is SnET2.

147. The method of claim 145, wherein the solvent or mixture of solvents is selected from dichloromethane, ether, dichloroethane, chloroform, toluene, and benzene.

148. The method of claim 145, wherein the precipitating solvent is selected from acetic acid, acetone, ethanol, methanol, dimethylformamide, and acetonitrile.

149. The method of claim 148, wherein the precipitating solvent is selected from acetic acid, acetone, and ethanol.

* * * * *

UNITED STATES PATENT AND TRADEMARK OFFICE
CERTIFICATE OF CORRECTION

PATENT NO.    : 6,462,192 B2
DATED         : October 8, 2002
INVENTOR(S)   : Byron C. Robinson and Barbara A. Garcia It is certified that error appears in the above-identified patent and that said Letters Patent is hereby corrected as shown below:

Column 51,
Lines 34-35, "coproporphyrn" should read -- coproporphyrin --.
Line 47, "chlorine a" should read -- chlorin, a --.

Column 53,
Line 33, "5,15diacrylate" should read -- 5,15-diacrylate --.

Column 56,
Line 34, "wherein the both the" should read -- wherein both the --.

Column 60,
Line 62, "tetrapyrroie" should read -- tetrapyrrole --.

Signed and Sealed this

Eleventh Day of February, 2003

JAMES E. ROGAN
*Director of the United States Patent and Trademark Office*